United States Patent
Nettenstrom

(10) Patent No.: US 11,123,501 B2
(45) Date of Patent: Sep. 21, 2021

(54) ELECTRONIC VAPOR PROVISION SYSTEM

(71) Applicant: NICOVENTURES HOLDINGS LIMITED, London (GB)

(72) Inventor: Matthew Joel Nettenstrom, London (GB)

(73) Assignee: Nicoventures Holdings Limited, London (GB)

( * ) Notice: Subject to any disclaimer, the term of this patent is extended or adjusted under 35 U.S.C. 154(b) by 261 days.

(21) Appl. No.: 16/087,000

(22) PCT Filed: Mar. 21, 2017

(86) PCT No.: PCT/GB2017/050782
§ 371 (c)(1),
(2) Date: Sep. 20, 2018

(87) PCT Pub. No.: WO2017/163045
PCT Pub. Date: Sep. 28, 2017

(65) Prior Publication Data
US 2019/0099561 A1 Apr. 4, 2019

(30) Foreign Application Priority Data

Mar. 24, 2016 (GB) .................................. 1605101
Jul. 21, 2016 (GB) .................................. 1612683

(51) Int. Cl.
*A24F 13/00* (2006.01)
*A61M 11/04* (2006.01)
(Continued)

(52) U.S. Cl.
CPC ........... *A61M 11/042* (2014.02); *A24F 40/40* (2020.01); *A24F 40/50* (2020.01); *A61M 15/06* (2013.01);
(Continued)

(58) Field of Classification Search
CPC ....................................................... A24F 47/00
(Continued)

(56) References Cited

U.S. PATENT DOCUMENTS 3,614,956 A   10/1971   Thornton et al.
3,888,253 A   6/1975    Watt et al.
(Continued)

FOREIGN PATENT DOCUMENTS

AT      508244 A4      12/2010
AU   2017236411 B2     6/2019
(Continued)

OTHER PUBLICATIONS

Application and File History for U.S. Appl. No. 16/087,019, filed Sep. 20, 2018. Inventors: Nettenstrom et al.
(Continued)

*Primary Examiner* — Phuong K Dinh
(74) *Attorney, Agent, or Firm* — Patterson Thuente Pedersen, P.A.

(57) ABSTRACT

A vapor provision system includes a cartridge part (cartomizer) including a vaporizer for generating a vapor from a vapor precursor material for inhalation by a user; and a device part (control unit) comprising a power supply, such as a battery, for supplying power to the vaporizer across an electrical interface established between the cartridge part and the device part when the cartridge part is coupled to the device part for use. The electrical interface is provided by sprung pins in one of the cartridge part and the device part and a circuit board with contact pads in the other of the cartridge part and the device part. The sprung pins and contact pads are arranged in cooperative alignment so that respective ones of the sprung pins are in biased contact with corresponding ones of contact pads when the cartridge part is coupled to the device part for use.

22 Claims, 6 Drawing Sheets

(51) Int. Cl.
*A61M 15/06* (2006.01)
*A24F 40/40* (2020.01)
*A24F 40/50* (2020.01)
*A61M 16/00* (2006.01)
*A24F 40/10* (2020.01)

(52) U.S. Cl.
CPC ...... *A24F 40/10* (2020.01); *A61M 2016/0015* (2013.01); *A61M 2205/3331* (2013.01); *A61M 2205/3368* (2013.01); *A61M 2205/3379* (2013.01); *A61M 2205/3653* (2013.01); *A61M 2205/8206* (2013.01)

(58) Field of Classification Search
USPC .................................................. 131/328–329
See application file for complete search history.

(56) References Cited

U.S. PATENT DOCUMENTS

| | | |
|---|---|---|
| 4,022,221 A | 5/1977 | Berger |
| D250,485 S | 12/1978 | Cuthbertson |
| 4,517,996 A | 5/1985 | Vester |
| 4,602,647 A | 7/1986 | Wiethaup et al. |
| 4,655,229 A | 4/1987 | Sensabaugh, Jr. et al. |
| D367,526 S | 2/1996 | Bignon |
| 5,564,442 A | 10/1996 | MacDonald et al. |
| D430,358 S | 8/2000 | Papiernik |
| D447,276 S | 8/2001 | Gustafson |
| 6,418,926 B1 | 7/2002 | Chawla |
| 6,446,880 B1 | 9/2002 | Schram et al. |
| D466,644 S | 12/2002 | Harel |
| D469,962 S | 2/2003 | Campbell et al. |
| D503,996 S | 4/2005 | Mabbutt |
| D504,947 S | 5/2005 | McAULEY |
| D505,514 S | 5/2005 | Liu |
| D514,222 S | 1/2006 | Anderson et al. |
| D518,171 S | 3/2006 | Anderson et al. |
| D560,793 S | 1/2008 | Pearl |
| D569,967 S | 5/2008 | Pearl |
| D572,406 S | 7/2008 | Masoud |
| D577,815 S | 9/2008 | Gokhale et al. |
| D579,544 S | 10/2008 | Birath et al. |
| D579,545 S | 10/2008 | Birath et al. |
| D579,546 S | 10/2008 | Birath et al. |
| D579,547 S | 10/2008 | Birath et al. |
| D579,548 S | 10/2008 | Birath et al. |
| D579,549 S | 10/2008 | Birath et al. |
| D579,550 S | 10/2008 | Birath et al. |
| D581,520 S | 11/2008 | Williams et al. |
| D583,463 S | 12/2008 | Wood et al. |
| D590,495 S | 4/2009 | Lulla et al. |
| D590,938 S | 4/2009 | Lulla et al. |
| D591,856 S | 5/2009 | Lulla et al. |
| D613,848 S | 4/2010 | Harvey |
| D614,285 S | 4/2010 | Birath et al. |
| D629,886 S | 12/2010 | Adamo et al. |
| D637,280 S | 5/2011 | Harvey |
| D637,281 S | 5/2011 | Harvey |
| D637,282 S | 5/2011 | Harvey |
| D639,414 S | 6/2011 | Berndt |
| D641,076 S | 7/2011 | Grunstad |
| D646,780 S | 10/2011 | Lulla et al. |
| D659,236 S | 5/2012 | Bobjer et al. |
| D670,374 S | 11/2012 | Bobjer et al. |
| D671,207 S | 11/2012 | Bobjer et al. |
| D684,254 S | 6/2013 | Zuyderhoudt |
| D684,684 S | 6/2013 | Grunstad |
| D692,997 S | 11/2013 | Lovell et al. |
| D693,963 S | 11/2013 | Akopyan |
| D700,227 S | 2/2014 | Kile |
| D700,738 S | 3/2014 | Rennick et al. |
| D710,002 S | 7/2014 | Valentine |
| D711,528 S | 8/2014 | Grunstad |
| D717,425 S | 11/2014 | Schuckmann |
| D726,364 S | 4/2015 | Weigensberg |
| D726,955 S | 4/2015 | Martin |
| D737,419 S | 8/2015 | Emarlou |
| D737,426 S | 8/2015 | Nakamura |
| 9,155,336 B2 | 10/2015 | Liu |
| D745,139 S | 12/2015 | Chen et al. |
| D745,660 S | 12/2015 | Gruntad et al. |
| D761,488 S | 7/2016 | Alarcon et al. |
| D769,438 S | 10/2016 | Crosby |
| D770,088 S | 10/2016 | Abadi et al. |
| D782,109 S | 3/2017 | King |
| D790,123 S | 6/2017 | Beer et al. |
| D790,125 S | 6/2017 | Beer et al. |
| D790,767 S | 6/2017 | Rush et al. |
| D799,750 S | 10/2017 | Parcevaux |
| 9,956,357 B2 | 5/2018 | Chen |
| 9,964,300 B2 | 5/2018 | Liu |
| D820,514 S | 6/2018 | Durand |
| D820,515 S | 6/2018 | Nettenstrom et al. |
| D822,193 S | 7/2018 | Nitta |
| 10,010,109 B2 | 7/2018 | Janardhan |
| 10,058,122 B2 | 8/2018 | Steingraber |
| D852,408 S | 6/2019 | Nettenstrom et al. |
| 10,653,186 B2 | 5/2020 | Verleur et al. |
| 2002/0040713 A1 | 4/2002 | Eisele et al. |
| 2003/0178024 A1 | 9/2003 | Allan et al. |
| 2003/0235538 A1 | 12/2003 | Zierenberg |
| 2004/0003820 A1 | 1/2004 | Iannuzzi |
| 2004/0025865 A1 | 2/2004 | Nichols et al. |
| 2004/0025877 A1 | 2/2004 | Crowder |
| 2004/0118936 A1 | 6/2004 | Schram et al. |
| 2004/0149283 A1 | 8/2004 | Hochrainer |
| 2004/0244810 A1 | 12/2004 | Henninger |
| 2005/0005934 A1 | 1/2005 | Harvey |
| 2005/0006273 A1 | 1/2005 | Chawla |
| 2005/0017017 A1 | 1/2005 | Crosby et al. |
| 2005/0022812 A1 | 2/2005 | Hrkach |
| 2005/0103336 A1 | 5/2005 | Nishibayashi et al. |
| 2005/0103337 A1 | 5/2005 | Hickey et al. |
| 2005/0115562 A1 | 6/2005 | Chawla |
| 2005/0205685 A1 | 9/2005 | Jones |
| 2005/0252511 A1 | 11/2005 | Pentafragas |
| 2005/0279357 A1 | 12/2005 | Wachtel |
| 2006/0102175 A1 | 5/2006 | Nelson |
| 2006/0157053 A1 | 7/2006 | Barney et al. |
| 2006/0157054 A1 | 7/2006 | Kuehn et al. |
| 2006/0163269 A1 | 7/2006 | Anderson et al. |
| 2006/0196518 A1 | 9/2006 | Hon |
| 2006/0237010 A1 | 10/2006 | De Boer et al. |
| 2006/0237016 A1 | 10/2006 | Wachtel |
| 2007/0045288 A1 | 3/2007 | Nelson |
| 2007/0052544 A1 | 3/2007 | Lintell |
| 2007/0102016 A1 | 5/2007 | Xiahou |
| 2007/0114305 A1 | 5/2007 | Yamaguchi et al. |
| 2007/0125765 A1 | 6/2007 | Nelson |
| 2007/0131805 A1 | 6/2007 | Yamaguchi et al. |
| 2007/0137645 A1 | 6/2007 | Eason et al. |
| 2007/0152086 A1 | 7/2007 | Yamaguchi et al. |
| 2007/0181123 A1 | 8/2007 | Houzego |
| 2007/0215149 A1 | 9/2007 | King et al. |
| 2007/0267031 A1 | 11/2007 | Hon |
| 2007/0267032 A1 | 11/2007 | Shan |
| 2008/0099015 A1 | 5/2008 | Pocock et al. |
| 2008/0116220 A1 | 5/2008 | Pocock et al. |
| 2008/0196718 A1 | 8/2008 | Connell et al. |
| 2008/0295832 A1 | 12/2008 | Geser et al. |
| 2008/0295834 A1 | 12/2008 | Thoemmes et al. |
| 2008/0314384 A1 | 12/2008 | Harris et al. |
| 2009/0084379 A1 | 4/2009 | Goeckner et al. |
| 2009/0165791 A1 | 7/2009 | Wendland |
| 2009/0194105 A1 | 8/2009 | Besseler et al. |
| 2009/0205656 A1 | 8/2009 | Nishibayashi et al. |
| 2009/0250056 A1 | 10/2009 | Pentafragas |
| 2009/0277446 A1 | 11/2009 | Walz |
| 2009/0283095 A1 | 11/2009 | Pocock et al. |
| 2009/0293888 A1 | 12/2009 | Williams et al. |
| 2009/0293892 A1 | 12/2009 | Williams et al. |
| 2009/0314291 A1 | 12/2009 | Anderson et al. |
| 2010/0024812 A1 | 2/2010 | Sugita et al. |

(56) References Cited

U.S. PATENT DOCUMENTS

| | | |
|---|---|---|
| 2010/0024814 A1 | 2/2010 | Sugita et al. |
| 2010/0059050 A1 | 3/2010 | Wachtel |
| 2010/0059052 A1 | 3/2010 | Davies et al. |
| 2010/0083962 A1 | 4/2010 | Von Schuckmann |
| 2010/0154795 A1 | 6/2010 | Pentafragas |
| 2010/0163042 A1 | 7/2010 | Bhowmick et al. |
| 2010/0189780 A1 | 7/2010 | Walz et al. |
| 2010/0192949 A1 | 8/2010 | Wright et al. |
| 2010/0242960 A1 | 9/2010 | Zangerle |
| 2010/0258120 A1 | 10/2010 | Colomb |
| 2010/0294278 A1 | 11/2010 | Mosier et al. |
| 2010/0313886 A1 | 12/2010 | Wachtel et al. |
| 2011/0011396 A1 | 1/2011 | Fang |
| 2011/0036346 A1 | 2/2011 | Cohen et al. |
| 2011/0041841 A1 | 2/2011 | Wachtel et al. |
| 2011/0067696 A1 | 3/2011 | Sato et al. |
| 2011/0094523 A1 | 4/2011 | Thorens et al. |
| 2011/0120463 A1 | 5/2011 | Esteve et al. |
| 2011/0120465 A1 | 5/2011 | Haerder et al. |
| 2011/0162642 A1 | 7/2011 | Akouka et al. |
| 2011/0174305 A1 | 7/2011 | Bunch et al. |
| 2011/0203586 A1 | 8/2011 | Egen et al. |
| 2011/0226236 A1 | 9/2011 | Buchberger |
| 2011/0232637 A1 | 9/2011 | Kaemper et al. |
| 2011/0271958 A1 | 11/2011 | Sawant |
| 2011/0277757 A1 | 11/2011 | Terry et al. |
| 2011/0277760 A1 | 11/2011 | Terry et al. |
| 2012/0037157 A1 | 2/2012 | Rohrschneider |
| 2012/0037158 A1 | 2/2012 | Wachtel et al. |
| 2012/0132205 A1 | 5/2012 | Meliniotis et al. |
| 2012/0247463 A1 | 10/2012 | Zoltan |
| 2012/0260917 A1 | 10/2012 | Bilgic |
| 2013/0047985 A1 | 2/2013 | Harris et al. |
| 2013/0074857 A1 | 3/2013 | Buchberger |
| 2013/0139815 A1 | 6/2013 | Colomb et al. |
| 2013/0152927 A1 | 6/2013 | Baillet et al. |
| 2013/0152928 A1 | 6/2013 | Kirniak |
| 2013/0174842 A1 | 7/2013 | Young et al. |
| 2013/0186398 A1 | 7/2013 | Baillet et al. |
| 2013/0192615 A1 | 8/2013 | Tucker et al. |
| 2013/0228191 A1 | 9/2013 | Newton |
| 2013/0233313 A1 | 9/2013 | Young et al. |
| 2013/0255679 A1 | 10/2013 | Andrade et al. |
| 2013/0269695 A1 | 10/2013 | Brouet et al. |
| 2013/0306065 A1 | 11/2013 | Thorens et al. |
| 2013/0340778 A1 | 12/2013 | Liu |
| 2014/0000601 A1 | 1/2014 | Arvidsson et al. |
| 2014/0007875 A1 | 1/2014 | Berg et al. |
| 2014/0076315 A1 | 3/2014 | Von Schuckmann |
| 2014/0083422 A1 | 3/2014 | Arvidsson et al. |
| 2014/0109921 A1 | 4/2014 | Chen |
| 2014/0123989 A1 | 5/2014 | LaMOTHE |
| 2014/0196716 A1 | 7/2014 | Liu |
| 2014/0196717 A1 | 7/2014 | Liu |
| 2014/0238422 A1 | 8/2014 | Plunkett et al. |
| 2014/0238424 A1 | 8/2014 | Macko et al. |
| 2014/0290653 A1 | 10/2014 | Colomb |
| 2014/0299125 A1 | 10/2014 | Buchberger |
| 2014/0318538 A1 | 10/2014 | Bilgic |
| 2014/0360514 A1 | 12/2014 | Zhu |
| 2014/0376895 A1 | 12/2014 | Han |
| 2015/0027454 A1 | 1/2015 | Li et al. |
| 2015/0027456 A1 | 1/2015 | Janardhan |
| 2015/0027457 A1 | 1/2015 | Janardhan |
| 2015/0059747 A1 | 3/2015 | Von Schuckmann |
| 2015/0068541 A1 | 3/2015 | Sears et al. |
| 2015/0080808 A1 | 3/2015 | Esteve et al. |
| 2015/0083129 A1 | 3/2015 | Colomb et al. |
| 2015/0096563 A1 | 4/2015 | Toksoz et al. |
| 2015/0107590 A1 | 4/2015 | Colomb |
| 2015/0114391 A1 | 4/2015 | Colomb et al. |
| 2015/0114393 A1 | 4/2015 | Von Schuckmann |
| 2015/0118895 A1 | 4/2015 | Zheng et al. |
| 2015/0122276 A1 | 5/2015 | Johnson et al. |
| 2015/0122277 A1 | 5/2015 | Frobisher et al. |
| 2015/0128938 A1 | 5/2015 | Colomb et al. |
| 2015/0128971 A1 | 5/2015 | Verleur et al. |
| 2015/0128977 A1 | 5/2015 | Li et al. |
| 2015/0144145 A1 | 5/2015 | Chang et al. |
| 2015/0144147 A1 | 5/2015 | Li et al. |
| 2015/0164142 A1 | 6/2015 | Li et al. |
| 2015/0174346 A1 | 6/2015 | Dhuppad et al. |
| 2015/0208730 A1 | 7/2015 | Li et al. |
| 2015/0216237 A1 | 8/2015 | Wensley et al. |
| 2015/0257446 A1 | 9/2015 | Chung |
| 2015/0282527 A1 | 10/2015 | Henry, Jr. |
| 2015/0297841 A1 | 10/2015 | Ono |
| 2015/0298893 A1 | 10/2015 | Welp |
| 2015/0305409 A1 | 10/2015 | Verleur et al. |
| 2015/0313287 A1 | 11/2015 | Verleur et al. |
| 2015/0314085 A1 | 11/2015 | Banoun |
| 2015/0320115 A1 | 11/2015 | Liu |
| 2015/0320116 A1 | 11/2015 | Bleloch et al. |
| 2015/0335075 A1 | 11/2015 | Minskoff et al. |
| 2015/0342256 A1 | 12/2015 | Chen |
| 2015/0343159 A1 | 12/2015 | Farr et al. |
| 2016/0001018 A1 | 1/2016 | Fink et al. |
| 2016/0001019 A1 | 1/2016 | Fink et al. |
| 2016/0007654 A1 | 1/2016 | Zhu |
| 2016/0015082 A1 | 1/2016 | Liu |
| 2016/0015912 A1 | 1/2016 | De Kruijf et al. |
| 2016/0021934 A1 | 1/2016 | Cadieux et al. |
| 2016/0022931 A1 | 1/2016 | Althorpe et al. |
| 2016/0045684 A1 | 2/2016 | Ono |
| 2016/0050975 A1 | 2/2016 | Worm et al. |
| 2016/0109115 A1 | 4/2016 | Lipowicz |
| 2016/0128386 A1 | 5/2016 | Chen |
| 2016/0143365 A1 | 5/2016 | Liu |
| 2016/0151589 A1 | 6/2016 | Ohrt et al. |
| 2016/0158470 A1 | 6/2016 | Esteve et al. |
| 2016/0175547 A1 | 6/2016 | Nakamura |
| 2016/0219936 A1 | 8/2016 | Alarcon |
| 2016/0264290 A1 | 9/2016 | Hafer et al. |
| 2016/0279354 A1 | 9/2016 | De Kruijf et al. |
| 2016/0287818 A1 | 10/2016 | Colomb et al. |
| 2016/0338411 A1 | 11/2016 | Liu |
| 2016/0346488 A1 | 12/2016 | Beller |
| 2016/0367767 A1 | 12/2016 | Cashman et al. |
| 2016/0375207 A1 | 12/2016 | Bhide et al. |
| 2017/0035117 A1 | 2/2017 | Lin |
| 2017/0056608 A1 | 3/2017 | McDerment et al. |
| 2017/0064999 A1 | 3/2017 | Perez et al. |
| 2017/0119057 A1 | 5/2017 | Liu |
| 2017/0127728 A1 | 5/2017 | Li et al. |
| 2017/0208866 A1 | 7/2017 | Liu |
| 2017/0231281 A1 | 8/2017 | Hatton et al. |
| 2017/0231282 A1 | 8/2017 | Bowen et al. |
| 2017/0280773 A1 | 10/2017 | Force |
| 2017/0280778 A1 | 10/2017 | Force |
| 2017/0325504 A1 | 11/2017 | Liu |
| 2017/0360092 A1 | 12/2017 | Althorpe et al. |
| 2018/0007960 A1 | 1/2018 | Suzuki et al. |
| 2018/0035718 A1 | 2/2018 | Liu |
| 2018/0213845 A1 | 8/2018 | Qiu |
| 2018/0220708 A1 | 8/2018 | Scott et al. |
| 2018/0228216 A1 | 8/2018 | Saygili |
| 2018/0352867 A1 | 12/2018 | Kane et al. |
| 2019/0022345 A1 | 1/2019 | Kotch |
| 2019/0046745 A1 | 2/2019 | Nettenstrom et al. |
| 2019/0053542 A1 | 2/2019 | Chen |
| 2019/0083720 A1 | 3/2019 | Leadley et al. |
| 2019/0098931 A1 | 4/2019 | Leadley et al. |
| 2019/0191764 A1* | 6/2019 | Lin ................... A24F 47/008 |
| 2019/0230991 A1 | 8/2019 | Liu et al. |
| 2020/0138117 A1 | 5/2020 | Rosser et al. |
| 2020/0146360 A1 | 5/2020 | Rosser |
| 2020/0154770 A1 | 5/2020 | Hepworth et al. |
| 2020/0281270 A1 | 9/2020 | Potter et al. |

(56) References Cited

U.S. PATENT DOCUMENTS

2020/0367557 A1 11/2020 Lin et al.
2020/0375263 A1 12/2020 Chen

FOREIGN PATENT DOCUMENTS

| | | |
|---|---|---|
| AU | 2017236563 B2 | 10/2019 |
| CA | 2505366 A1 | 10/2006 |
| CL | 2018002640 A1 | 12/2018 |
| CL | 2018002657 A1 | 12/2018 |
| CL | 2018002658 A1 | 12/2018 |
| CN | 2698098 Y | 5/2005 |
| CN | 2827020 Y | 10/2006 |
| CN | 300865525 | 9/2007 |
| CN | 300840847 | 10/2008 |
| CN | 300867097 | 12/2008 |
| CN | 101400397 A | 4/2009 |
| CN | 101468218 A | 7/2009 |
| CN | 101574552 A | 11/2009 |
| CN | 301347038 S | 12/2009 |
| CN | 301433957 S | 6/2010 |
| CN | 201791251 U | 4/2011 |
| CN | 202085710 U | 12/2011 |
| CN | 302012774 S | 3/2012 |
| CN | 302216014 S | 12/2012 |
| CN | 103118726 A | 5/2013 |
| CN | 103237570 A | 8/2013 |
| CN | 302926278 S | 1/2014 |
| CN | 203457805 U | 3/2014 |
| CN | 203492795 U | 3/2014 |
| CN | 203523806 U | 4/2014 |
| CN | 203575649 U | 5/2014 |
| CN | 203676136 U | 7/2014 |
| CN | 203676140 U | 7/2014 |
| CN | 203872998 U | 10/2014 |
| CN | 104254258 A | 12/2014 |
| CN | 204015104 U | 12/2014 |
| CN | 104544567 A | 4/2015 |
| CN | 104544570 A | 4/2015 |
| CN | 303162040 S | 4/2015 |
| CN | 303192526 S | 4/2015 |
| CN | 104605482 A | 5/2015 |
| CN | 204317491 U | 5/2015 |
| CN | 303227659 S | 5/2015 |
| CN | 303417607 | 5/2015 |
| CN | 104720114 A | 6/2015 |
| CN | 303234670 S | 6/2015 |
| CN | 303250845 S | 6/2015 |
| CN | 303442703 S | 6/2015 |
| CN | 303535276 S | 6/2015 |
| CN | 104770882 A | 7/2015 |
| CN | 204426686 U | 7/2015 |
| CN | 204444245 U | 7/2015 |
| CN | 204483034 U | 7/2015 |
| CN | 303273075 S | 7/2015 |
| CN | 303279026 S | 7/2015 |
| CN | 303300421 S | 7/2015 |
| CN | 303300422 S | 7/2015 |
| CN | 104824846 A | 8/2015 |
| CN | 204519363 U | 8/2015 |
| CN | 303322969 S | 8/2015 |
| CN | 303322971 S | 8/2015 |
| CN | 303322985 S | 8/2015 |
| CN | 303341926 S | 8/2015 |
| CN | 303350911 S | 8/2015 |
| CN | 104921308 A | 9/2015 |
| CN | 204617062 U | 9/2015 |
| CN | 303361183 S | 9/2015 |
| CN | 303380240 S | 9/2015 |
| CN | 303380242 S | 9/2015 |
| CN | 303380243 S | 9/2015 |
| CN | 303380252 S | 9/2015 |
| CN | 303417611 S | 10/2015 |
| CN | 105011380 A | 11/2015 |
| CN | 204742629 U | 11/2015 |
| CN | 303470028 S | 11/2015 |
| CN | 105455197 A | 4/2016 |
| CN | 105455197 B | 1/2019 |
| DE | 95102980001 | 9/1996 |
| DE | 96072850001 | 4/1997 |
| DE | 96072850002 | 4/1997 |
| DE | 499019970001 | 7/1999 |
| DE | 499019970002 | 7/1999 |
| DE | 400039090001 | 8/2000 |
| DE | 401071010001 | 2/2002 |
| DE | 402003030001 | 8/2002 |
| DE | 402093100001 | 3/2003 |
| DE | 402093100002 | 3/2003 |
| DE | 402093100003 | 3/2003 |
| DE | 402093100004 | 3/2003 |
| DE | 402093100005 | 3/2003 |
| DE | 403019480001 | 7/2003 |
| DE | 202013010929 U1 | 12/2013 |
| DE | 96072850003 | 3/2016 |
| EA | 019736 B1 | 5/2014 |
| EM | 0001050440001 | 6/2003 |
| EM | 0001050440002 | 6/2003 |
| EM | 0005457690001 | 6/2006 |
| EM | 0007369620001 | 6/2007 |
| EM | 0007369620002 | 6/2007 |
| EM | 0007369620003 | 6/2007 |
| EM | 0007369620004 | 6/2007 |
| EM | 0007369620005 | 6/2007 |
| EM | 0007369620006 | 6/2007 |
| EM | 0007369620007 | 6/2007 |
| EM | 0007369620008 | 6/2007 |
| EM | 0008611410001 | 1/2008 |
| EM | 0015105870001 | 5/2009 |
| EM | 0015105870002 | 5/2009 |
| EM | 0013233070007 | 4/2012 |
| EM | 0013233070008 | 4/2012 |
| EM | 0013233070009 | 4/2012 |
| EM | 0013233070010 | 4/2012 |
| EM | 0013233070011 | 4/2012 |
| EM | 0013233070012 | 4/2012 |
| EM | 0024296960003 | 3/2014 |
| EM | 0024296960004 | 3/2014 |
| EM | 0014157800001 | 7/2014 |
| EM | 0014157800002 | 7/2014 |
| EM | 0014157800003 | 7/2014 |
| EM | 0014157800004 | 7/2014 |
| EM | 0014157800005 | 7/2014 |
| EM | 0014157800006 | 7/2014 |
| EM | 0014157800007 | 7/2014 |
| EM | 0014157800008 | 7/2014 |
| EM | 0014157800009 | 7/2014 |
| EM | 0026967650003 | 5/2015 |
| EM | 0029228640002 | 12/2015 |
| EP | 1496858 A1 | 1/2005 |
| EP | 2319334 A1 | 5/2011 |
| EP | 2460424 A1 | 6/2012 |
| EP | 1496858 B1 | 8/2013 |
| EP | 2801270 A2 | 11/2014 |
| EP | 2843794 A1 | 3/2015 |
| EP | 2870888 A1 | 5/2015 |
| EP | 2875740 A2 | 5/2015 |
| EP | 2878213 A1 | 6/2015 |
| EP | 3039976 A1 | 7/2016 |
| EP | 3103355 A1 | 12/2016 |
| FR | 970852009 | 8/1997 |
| FR | 983203001 | 10/1998 |
| FR | 956833001 | 1/1999 |
| FR | 001967001 | 7/2000 |
| FR | 007595001 | 4/2001 |
| FR | 007595002 | 4/2001 |
| FR | 011038001 | 5/2001 |
| FR | 011152001 | 5/2001 |
| FR | 011154001 | 5/2001 |
| FR | 201125490001 | 7/2011 |
| FR | 201127120001 | 7/2011 |
| FR | 201127120002 | 7/2011 |
| FR | 201127120003 | 7/2011 |
| FR | 2962339 A1 | 1/2012 |
| FR | 20124875012 | 8/2013 |
| FR | 3039039 A1 | 1/2017 |

(56) References Cited

FOREIGN PATENT DOCUMENTS

| | | |
|---|---|---|
| GB | 488340 A | 7/1938 |
| GB | 911405 A | 11/1962 |
| GB | 2047060 A | 11/1980 |
| GB | 2115679 A | 9/1983 |
| GB | 1029228 | 4/1986 |
| GB | 2191718 A | 12/1987 |
| GB | 2048538 | 11/1995 |
| GB | 2055446 | 8/1996 |
| GB | 2075058 | 9/1998 |
| GB | 2093858 | 8/2000 |
| GB | 2093859 | 8/2000 |
| GB | 2412876 A | 10/2005 |
| GB | 4020185 | 11/2011 |
| GB | 2504077 A | 1/2014 |
| GB | 2508520 A | 6/2014 |
| GB | 2515562 A | 12/2014 |
| GB | 4041108 | 6/2015 |
| IT | 1993MIO0001280003 | 3/1993 |
| IT | 2000TOO000235004 | 9/2000 |
| IT | 2000TOO000235006 | 9/2000 |
| IT | 2000TOO0002350001 | 9/2000 |
| IT | 2000TOO0002350003 | 9/2000 |
| IT | 2002TOO0002140001 | 9/2002 |
| IT | 2002TOO0002140002 | 9/2002 |
| IT | 2002TOO0002140003 | 9/2002 |
| IT | 2002TOO0002140004 | 9/2002 |
| JP | H0712849 Y2 | 3/1995 |
| JP | H08322934 A | 12/1996 |
| JP | H08511966 A | 12/1996 |
| JP | 2005525393 A | 8/2005 |
| JP | 2007501271 A | 1/2007 |
| JP | 2007502683 A | 2/2007 |
| JP | 2007511437 A | 5/2007 |
| JP | 2009536062 A | 10/2009 |
| JP | 2013507976 A | 3/2013 |
| JP | 2013545473 A | 12/2013 |
| JP | 2014519850 A | 8/2014 |
| JP | D1575098 S | 3/2017 |
| JP | 6621154 B2 | 12/2019 |
| KR | 100495099 B1 | 11/2005 |
| KR | 20120098343 A | 9/2012 |
| KR | 101256914 B1 | 4/2013 |
| KZ | KZ30993 B | 3/2016 |
| RU | 115629 U1 | 5/2012 |
| RU | 122000 U1 | 11/2012 |
| RU | 132954 U1 | 10/2013 |
| RU | 2536032 C2 | 12/2014 |
| RU | 2698528 C1 | 8/2019 |
| WO | WO-DM264451 | 6/1993 |
| WO | WO-DM0264451 | 6/1996 |
| WO | WO-9912596 A1 | 3/1999 |
| WO | WO-03095005 A1 | 11/2003 |
| WO | WO-2004080216 A1 | 9/2004 |
| WO | WO-2007007110 A1 | 1/2007 |
| WO | WO-2009092520 A1 | 7/2009 |
| WO | WO-2009092653 A1 | 7/2009 |
| WO | WO-2009152651 A1 | 12/2009 |
| WO | WO-2010114504 A1 | 10/2010 |
| WO | WO-2012004512 A1 | 1/2012 |
| WO | WO-2012004514 A1 | 1/2012 |
| WO | WO-2012004518 A1 | 1/2012 |
| WO | WO-2012047181 A1 | 4/2012 |
| WO | WO-2013083631 A1 | 6/2013 |
| WO | WO-2013118299 A1 | 8/2013 |
| WO | WO-2014066730 A1 | 5/2014 |
| WO | WO-2014135224 A1 | 9/2014 |
| WO | WO-2014159250 A1 | 10/2014 |
| WO | WO-2014201432 A1 | 12/2014 |
| WO | WO-2014204417 A1 | 12/2014 |
| WO | WO-2015006838 A1 | 1/2015 |
| WO | WO-2015022436 A1 | 2/2015 |
| WO | WO-2015026081 A1 | 2/2015 |
| WO | WO-2015073564 A1 | 5/2015 |
| WO | WO-2015112750 A1 | 7/2015 |
| WO | WO-2015113743 A1 | 8/2015 |
| WO | WO-2015117700 A1 | 8/2015 |
| WO | WO-2015166239 A1 | 11/2015 |
| WO | WO-2015173303 A1 | 11/2015 |
| WO | WO-2015175568 A1 | 11/2015 |
| WO | WO-2015190810 A1 | 12/2015 |
| WO | WO-2016005600 A1 | 1/2016 |
| WO | WO-2016014652 A1 | 1/2016 |
| WO | WO-2016079410 A1 | 5/2016 |
| WO | WO-2016107764 A2 | 7/2016 |
| WO | WO-2016107767 A1 | 7/2016 |
| WO | WO-2016109965 A1 | 7/2016 |
| WO | WO-2016118005 A1 | 7/2016 |
| WO | WO-2016122417 A1 | 8/2016 |
| WO | WO-2016150019 A1 | 9/2016 |
| WO | WO-2016159919 A1 | 10/2016 |
| WO | WO-2017013130 A1 | 1/2017 |
| WO | WO-DM094223001 | 1/2017 |
| WO | WO-2017024799 A1 | 2/2017 |
| WO | WO-2017163044 A1 | 9/2017 |
| WO | WO-2017163045 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017206211 A1 | 12/2017 |

OTHER PUBLICATIONS

Application and Filing Receipt for Design U.S. Appl. No. 29/573,612, filed Aug. 8, 2016, Inventors: Nettenstrom et al., 36 pages.
Application and Filing Receipt for Design U.S. Appl. No. 29/590,640, filed Jan. 12, 2017, Inventors: Nettenstrom et al., 18 pages.
Decision for Korean Application No. 3020160038357_M002 dated Dec. 14, 2016., 3 pages.
Decision dated Mar. 14, 2017 for Ukrainian Application No. S201601341,7 pages.
Decision to Grant a Patent dated Oct. 23, 2019 for Japanese Application No. 2018-545824, 5 pages.
Decision to Grant dated Mar. 27, 2019 for Russian Application No. 2018133622, 14 pages.
Decision to Grant dated May 30, 2019 for Russian Application No. 2018132701, 14 pages.
Decision to Grant dated Aug. 15, 2017 for Russian Application No. 201650539349, 4 pages.
Decision to Grant dated Aug. 28, 2017 for Russian Application No. 201750018449, 4 pages.
Electronic Cigarette | Vype Pebble | Govype, post date n/a, (c)n/a, govype.com, Aug. 30, 2017, https://www.govype.com/uk/vype-pebble-starter-kit. 2 pages.
Examination Report for Canadian Application No. 169756, dated Nov. 17, 2016, 1 page.
Formalities Notice No. 1 for Australian Design Application No. AU201614224, dated Aug. 9, 2016., 2 pages.
Formalities Notice No. 1 for Australian Design Application No. 201614225, dated Aug. 9, 2016, 2 pages.
Innokin EQ Pod System Vape Kit by vapeclub. dated 2018. found online [Sep. 24, 2018] https://www.vapeclub.co.uk/pods-and-closed-system-vape-starter—kits/innokin-eq-pod-system-vape-kit.html, 6 pages.
International Preliminary Reporton Patentability for Application No. PCT/GB2017/050787, dated Feb. 27, 2018, 12 pages.
International Search Report and Written Opinion for Application No. PCT/GB2017/050787, dated Jul. 3, 2017, 12 pages.
International Preliminary Report on Patentability for Application No. PCT/GB2017/050783, dated Jul. 6, 2018, 13 pages.
International Search Report and Written Opinion for Application No. PCT/GB2017/050783, dated Jun. 9, 2017, 15 pages.
International Preliminary Examining Authority for Application No. PCT/GB2017/050783, dated Jun. 12, 2018, 6 pages.
International Preliminary Reporton Patentability for Application No. PCT/GB2017/050781, dated Feb. 27, 2018, 13 pages.
International Preliminary Reporton Patentability for Application No. PCT/GB2017/050782, dated 19, Jun. 2018, 14 pgs.
International Preliminary Reporton Patentability for Application No. PCT/GB2017/050788, dated Aug. 3, 2018, 14 pages.

(56) References Cited

OTHER PUBLICATIONS

International Preliminary Reporton Patentability for Application No. PCT/GB2017/050789, dated Jul. 11, 2018, 13 pages.
International Search Report and Written Opinion for Application No. PCT/GB2017/050781 dated Jun. 14, 2017.
International Search Report and Written Opinion for Application No. PCT/GB2017/050782, dated 14, Jun. 2017, 11 pgs.
International Search Report and Written Opinion for Application No. PCT/GB2017/050788, dated Jun. 7, 2017, 13 pages.
International Search Report and Written Opinion for Application No. PCT/GB2017/050789, dated Jun. 7, 2017, 9 pages.
International Second Written Opinion for PCT Application No. PCT/GB2017/050788, dated Mar. 7, 2018, 9 pages.
JustFog C601 Pod System Vape Kit by vapeclub. dated 2018. found online [Sep. 24, 2018] https://www.vapeclub.co.uk/pods-and-closed-system-vape-starter-kits/justfog-c601-pod-system-vape-kit.html, 6 pages.
Notice of Allowance for Chinese Application No. 201630632827.4, dated Feb. 24, 2017, 2 pages.
Notice of Allowance for Japanese Application No. 2016016955, dated Feb. 14, 2017, 2 pages.
Notice of Allowance for Japanese Application No. 2016016956, dated Feb. 14, 2017, 2 pages.
Notice of Allowance for Japanese Application No. 2017-000313, dated Dec. 19, 2017, 3 pages.
Notice of Issuance for Chinese Application No. 201630370608.3, dated Dec. 30, 2016, 3 pages.
Notice of Reason for Refusal for Japanese Application No. 2018-548027 dated Dec. 10, 2019, 10 pages.
Notice of Reason for Refusal for Japanese Application No. 2018-548374 dated Oct. 1, 2019, 8 pages.
Office Action dated Jun. 1, 2020 for Chinese Application No. 201780019532.1, 46 pages.
Office Action dated May 20, 2020 for Chinese Application No. 201780018952.8, 21 pages.
Office Action for Canadian Application No. 3,018,460, dated Jul. 23, 2019, 6 pages.
Office Action for Chinese Application No. 201630370608.3, dated Nov. 1, 2016, 1 page.
Office Action for Japanese Application No. 2017-000313, dated Aug. 29, 2017, 4 pages.
Office Action dated Jan. 7, 2020 for Japanese Application No. 2018-549184, 14 pages.
Office Action dated Oct. 14, 2019 for Chilean Application No. 201802657, 16 pages.
Office Action dated Oct. 14, 2019 for Chilean Application No. 201802658, 18 pages.
Office Action dated Feb. 17, 2020 for Chilean Application No. 201802640, 15 pages.
Office Action dated Oct. 17, 2019 for Korean Application No. 10-2018-7038106, 17 pages.
Office Action dated Dec. 21, 2018 for Australian Application No. 2017236563, 2 pages.
Office action dated May 26, 2020 for Japanese Application No. 2018-545821, 8 pages.
Office Action dated Apr. 29, 2019 for Russian Application No. 2018133234, 14 pages.
Office Action dated Jun. 29, 2020 for Chinese Application No. 201780018542.3, 12 pages.
Office Action dated Mar. 30, 2020 for Korean Application No. 10-2018-7027563, 21 pages.
Office Action dated Feb. 21, 2017 for Russian Application No. 2016505393.
Office Action dated Jan. 13, 2017 for Ukrainian Application No. S201601341, 1 pages.
Office Action dated Nov. 23, 2016 for Mexican Application No. MX/f/2016/002430, 1 pages.
Office Action dated Oct. 6, 2016 for Russian Application No. 2016503052, 2 pages.
Search Report dated Jun. 10, 2019 for Russian Application No. 2018133541, 2 pages.
Search Report dated Aug. 11, 2016 for Great Britain Application No. 1605104.7, 5 pages.
Search Report dated Aug. 16, 2016 for Great Britain Application No. 1605103.9, 4 pages.
Search Report dated Aug. 25, 2016 for Great Britain Application No. 1605100.5, 3 pages.
Search Report dated Aug. 3, 2016 for Great Britain Application 1605106.2, 5 pages.
Search Report dated Feb. 9, 2016 for Great Britain Application No. GB1517088.9, 3 pages.
Search Report dated Jun. 9, 2017 for Great Britain Application No. 1612684.9, 4 pages.
Search Report under Section 17(5) dated Jul. 28, 2016 for Great Britain Application No. 1605101.3, 3 pages.
Smoant S8 Ultra-Portable System Kit _ Premium Electronic Cigarette by wicked vapor, mailed 2018, found online on Sep. 24, 2018, at https://wicked-vapor.com/products/smoant-s8-ultra-portable-system-kit, 2 pages.
U.S. Appl. No. 16/086,997, filed Sep. 20, 2018, Nettenstrom et al., Inventor(s), 43 pages.
U.S. Appl. No. 16/087,005, filed Sep. 20, 2018, Nettenstrom et al., Inventor(s), 37 pages.
U.S. Appl. No. 16/087,012, filed Sep. 20, 2018, Nettenstrom et al., Inventor(s), 39 pages.
U.S. Appl. No. 16/087,021, filed Sep. 20, 2018, Nettenstrom et al., Inventor(s), 27 pages.
Vincent V., "Renova Vapor Zero vape Pod Kit", mailed May 29, 2018, found online on Sep. 24, 2018, https://www.e-cigarette-forum.com/threads/renova-vapor-zero-vape-pod-kit-hqd-comma-vape-pod-kit-wismec-hiflask-pod-kit.865421/.
Written Opinion of the International Preliminary Examining Authority for Application No. PCT/GB2017/050783, dated Mar. 2, 2018, 6 pages.

* cited by examiner

ELECTRONIC VAPOR PROVISION SYSTEM

PRIORITY CLAIM

The present application is a National Phase entry of PCT Application No. PCT/GB2017/050782, filed Mar. 21, 2017, which claims priority from GB Patent Application No. 1605101.3, filed Mar. 24, 2016, and GB Patent Application No. 1612683.1, filed Jul. 21, 2016, each of which is hereby fully incorporated herein by reference.

FIELD

The present disclosure relates to electronic vapor provision systems such as nicotine delivery systems (e.g. electronic cigarettes and the like), and approaches for establishing electrical connections in such systems.

BACKGROUND

Electronic vapor provision systems such as electronic cigarettes (e-cigarettes) generally contain a vapor precursor material, such as a reservoir of a source liquid containing a formulation, typically including nicotine, or a solid material such a tobacco-based product, from which a vapor is generated for inhalation by a user, for example through heat vaporization. Thus, a vapor provision system will typically comprise a vapor generation chamber containing a vaporizer, e.g. a heating element, arranged to vaporize a portion of precursor material to generate a vapor in the vapor generation chamber. As a user inhales on the device and electrical power is supplied to the vaporizer, air is drawn into the device through inlet holes and into the vapor generation chamber where the air mixes with the vaporized precursor material. There is a flow path connecting between the vapor generation chamber and an opening in the mouthpiece so the incoming air drawn through the vapor generation chamber continues along the flow path to the mouthpiece opening, carrying some of the vapor with it, and out through the mouthpiece opening for inhalation by the user.

It is common for vapor provision systems to comprise two main functional parts, namely a reusable part and disposable/replaceable cartridge part. Typically the cartridge part will comprise the consumable aerosol precursor material and the vaporizer, while the reusable device part will comprise longer-life items, such as a rechargeable battery, device control circuitry, activation sensors and user interface features. The reusable part may also be referred to as a control unit or battery section and the replaceable cartridge part may also be referred to as a cartomizer.

The control unit and cartomizer are mechanically coupled together at an interface for use, for example using a screw thread or bayonet fixing. When the vapor precursor material in a cartomizer is exhausted, or the user wishes to switch to a different cartomizer having a different vapor precursor material, the cartomizer may be removed from the control unit and a replacement cartomizer may be attached to the device in its place.

When the cartomizer and the controller unit are coupled together for use, an electrical connection/interface is established between them to allow the supply of electrical power from the battery in the control unit to the vaporizer in the cartomizer. Known techniques for establishing an electrical connection between the control unit and cartomizer include plug-and-socket type configurations and approaches based around bespoke contact structures (e.g. sprung steel ribbons) which connect when the two device parts are joined together for use. One drawback of known approaches is the relative structural complexity associated with these approaches can lead to increased manufacturing costs and increased risk of failure during use, for example leading to a poor connection (i.e. high resistance) or no connection being established when a cartridge part is coupled to a device part. Poor connections can be particularly problematic in the field of vapor provision systems because these typically operate with relatively high currents, for example of the order of numbers of amps.

Alternative arrangements for establishing the electrical connections between separable parts of vapor provision systems, such as electronic cigarettes, are therefore of interest.

SUMMARY

According to a first aspect of certain embodiments there is provided a vapor provision system comprising a control unit and a detachable cartridge; wherein the cartridge comprises a vaporizer for generating a vapor from a vapor precursor material for inhalation by a user; and the control unit comprises a power supply for supplying electrical power to the vaporizer across an electrical interface established between the control unit and the cartridge when the cartridge is coupled to the control unit for use; wherein the electrical interface is provided by contacts in one of the control unit and the cartridge and a contact board with contact pads in the other of the control unit and the cartridge, wherein the contacts and contact pads are arranged in cooperative alignment so that respective ones of the contacts are biased into contact with corresponding ones of contact pads when the cartridge is coupled to the control unit for use.

According to another aspect of certain embodiments there is provided a cartridge for a vapor provision system, wherein the cartridge comprises a vaporizer for generating a vapor from a vapor precursor material for inhalation by a user and is detachably couplable to a power supply for supplying electrical power to the vaporizer across an electrical interface established between the cartridge and the power supply when the cartridge is coupled to the power supply for use; wherein the electrical interface is provided by contacts in one of the power supply and the cartridge and a contact board with contact pads in the other of the power supply and the cartridge, wherein the contacts and contact pads are arranged in cooperative alignment so that respective ones of the contacts are biased into contact with corresponding ones of contact pads when the cartridge is coupled to the power supply for use.

According to another aspect of certain embodiments there is provided a control unit for a vapor provision system comprising the control unit and a detachable cartridge comprising a vaporizer for generating a vapor from a vapor precursor material for inhalation by a user, wherein the control unit comprises a power supply for supplying electrical power to the vaporizer across an electrical interface established between the control unit and the cartridge when the cartridge is coupled to the control unit for use; wherein the electrical interface is provided by contacts in one of the control unit and the cartridge and a contact board with contact pads in the other of the control unit and the cartridge, wherein the contacts and contact pads are arranged in cooperative alignment so that respective ones of the contacts are biased into contact with corresponding ones of contact pads when the cartridge is coupled to the control unit for use.

According to another aspect of certain embodiments there is provided a vapor provision means comprising control unit means and detachable cartridge means; wherein the cartridge means comprises vaporizer means for generating a vapor from a vapor precursor material for inhalation by a user; and the control unit means comprises power supply means for supplying electrical power to the vaporizer across electrical interface means established between the control unit means and the cartridge means when the cartridge means is coupled to the control unit means for use; wherein the electrical interface means is provided by contact means in one of the control unit means and the cartridge means and contact board with contact pad means in the other of the control unit means and the cartridge means, wherein the contact means and contact pad means are arranged in cooperative alignment so that respective ones of the contact means are biased into contact with corresponding ones of contact pad means when the cartridge means is coupled to the control unit means for use.

According to another aspect of certain embodiments there is provided a method of establishing an electrical connection between a control unit and a detachable cartridge in a vapor provision system, wherein the method comprises providing one of the control unit and the detachable cartridge with contacts and the other of the control unit and the detachable cartridge with a contact board with contact pads arranged, wherein the contacts and contact board are arranged so the contacts and contact pads are in cooperative alignment so that respective ones of the contacts are biased into contact with corresponding ones of contact pads when the cartridge is coupled to the control unit for use, and coupling the cartridge to the control unit to establish the electrical connection.

According to another aspect of certain embodiments there is provided a contact board for providing an electrical interface in a vapor provision system between a control unit and a detachable cartridge, wherein the contact board comprises electrical contact pads provided on a surface of an insulating substrate.

These and further aspects of certain embodiments are set out in the appended independent and dependent claims. It will be appreciated that features of the dependent claims may be combined with each other and features of the independent claims in combinations other than those explicitly set out in the claims. Furthermore, the approaches described herein are not restricted to specific embodiments such as the examples set out below, but include and contemplate any appropriate combinations of features presented herein. For example, a vapor provision system may be provided in accordance with approaches described herein which includes any one or more of the various features described below as appropriate.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to aerosol provision systems, also referred to as vapor provision systems, such as e-cigarettes. Throughout the following description the term "e-cigarette" or "electronic cigarette" may sometimes be used; however, it will be appreciated this term may be used interchangeably with aerosol (vapor) provision system and electronic aerosol (vapor) provision system.

Figure 1:
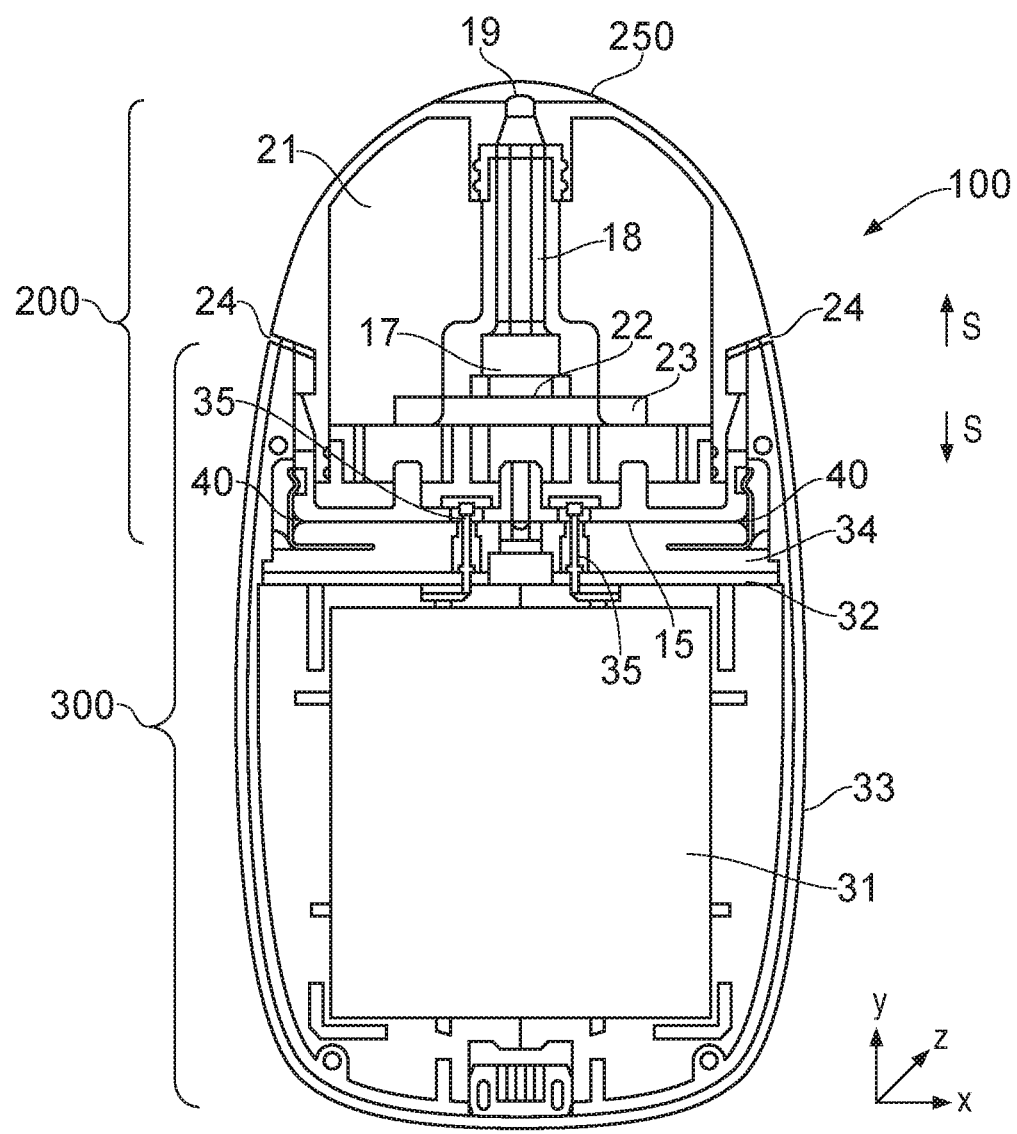
FIG. 1 schematically represents a cross-section view of a vapor provision system in accordance with certain embodiments of the disclosure.
Figure 4:
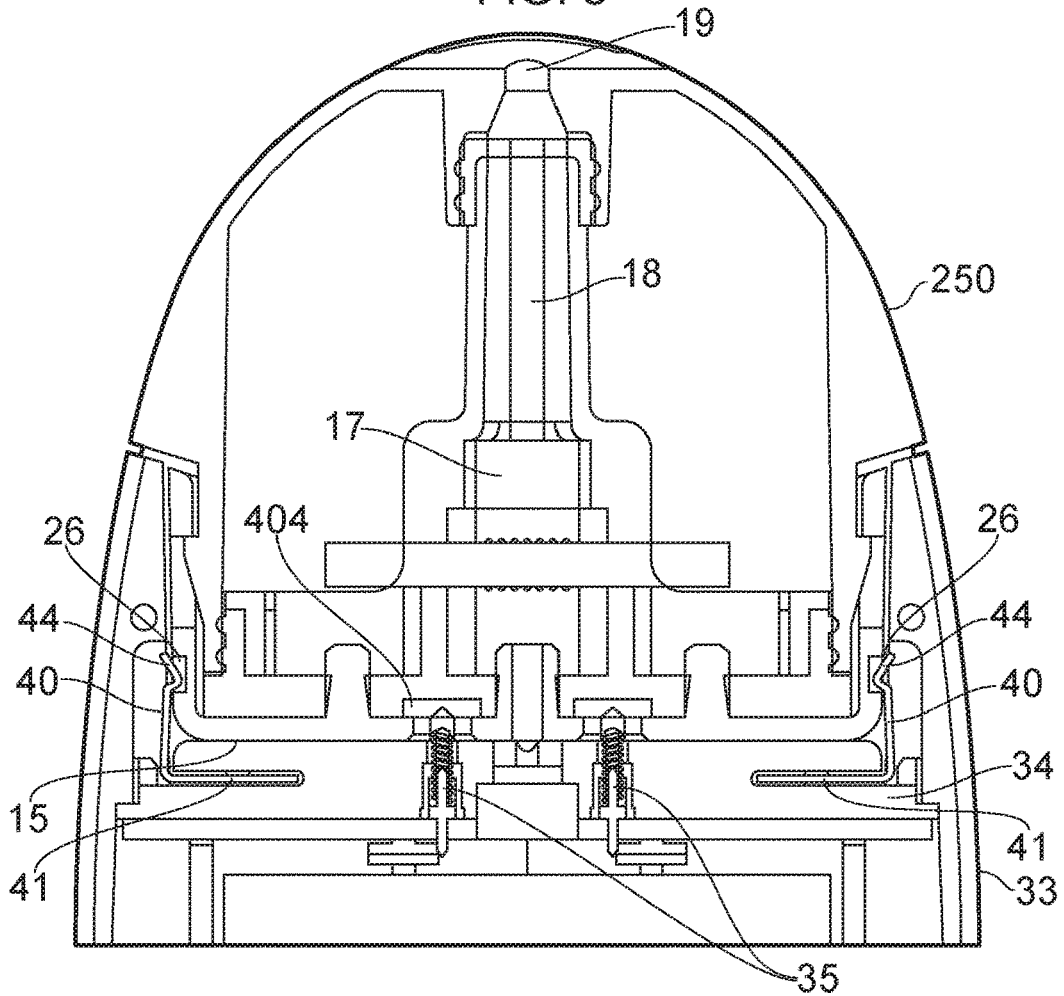
FIG. 4 represents a cross-section view of some components of the vapor provision system represented in FIG. 1 with a magnified scale.

FIG. 1 is a cross-sectional view through an example e-cigarette 100 in accordance with some embodiments of the disclosure. A magnified view of an upper part of the e-cigarette represented in FIG. 1 is presented in FIG. 4. The e-cigarette 100 comprises two main components, namely a cartomizer 200 and a control unit 300.

The cartomizer 200 includes a reservoir 21 containing a supply of liquid, a heater 22 to act as an atomizer or vaporizer, and a mouthpiece 250. In this example the heater 22 comprises a nickel chrome alloy (Cr20Ni80) wire. The liquid in the reservoir 21 (sometimes referred to as the e-liquid or source liquid) typically includes nicotine in an appropriate solvent, and may include further constituents, for example, to aid aerosol formation, and/or for additional flavoring. The cartomizer 200 further includes a wick 23, which in this example comprises a glass fiber bundle, or a similar facility to transport an amount of liquid from the reservoir 21 to a heating location on or adjacent the heater 22. The vaporizer (heater) 22 is located in a vapor generation chamber 17. The vapor generation chamber 17 is arranged in an air flow path that extends from air inlets/ventilation slots 24 provided at the joint between the cartomizer 200 and control unit 300, into the cartomizer 200 and through the vapor generation chamber 17 past the heater (vaporizer) 22, and along an air channel 18 providing fluid communication between the vapor generation chamber 17 and a vapor outlet 19 provided in the mouthpiece 250.

The control unit 300 includes within a housing 33 a re-chargeable cell or battery 31 to provide power to the e-cigarette 100 and a control printed circuit board 32 (PCB) comprising circuitry for generally controlling the operation of the e-cigarette 100, which may be undertaken in accordance with generally conventional techniques. Although not apparent in FIG. 1, the control unit 300 may comprise further circuit boards for providing functionality associated with the operation of the aerosol provision system. When the heater 22 receives power from the battery 31, e.g. as controlled by the control PCB 32, the heater 22 vaporizes a portion of liquid from the wick 23 to create a vapor in the vapor generation chamber 17, which is mixed with incoming air from the ventilation slots 24 and drawn along the air channel 18 and out through the vapor outlet 19 into the mouth of a user inhaling on the e-cigarette 100.

For ease of reference, x- and y-axes are included in FIG. 1. The x-axis corresponds to the width of the e-cigarette 100 (from side to side as shown in FIG. 1), while the y-axis corresponds to the height of the e-cigarette 100 (top to bottom as shown in FIG. 1), where in the orientation shown in FIG. 1 the cartomizer 200 represents an upper portion of the e-cigarette 100 and the control unit 300 represents a lower portion of the e-cigarette 100. Additionally, there is a z-axis which is perpendicular to the x- and y-axes shown in FIG. 1 (into the plane of the FIG. 1). The z-axis corresponds to the depth or thickness of the e-cigarette 100. In this example, the depth of the e-cigarette 100 is significantly less than the width of the e-cigarette 100, resulting in a generally flat or planar configuration (in the x-y plane). Accordingly, the z-axis can be considered as extending from face to face of the e-cigarette 100, where one face may be regarded (arbitrarily) as the front face of the e-cigarette 100 and the opposing face as the back face of the e-cigarette 100, the front and back faces being substantially parallel to the plane of FIG. 1. By way of a specific example, the electronic cigarette 100 may have a length (along the y-axis) of around 70 mm, a width (along the x-axis) of around 35 mm and a thickness (along the z-axis) of around 14 mm. However, it will be appreciated the principles described herein may be equally applied to electronic cigarettes having generally different shapes and sizes.

The cartomizer 200 and the control unit 300 are detachable from one another by separation in a direction parallel to the y-axis, indicated in FIG. 1 by the arrows S, but are joined together (as in FIG. 1) when the device 100 is in use so as to provide mechanical and electrical connectivity between the cartomizer 200 and the control unit 300. When the e-liquid in the cartomizer reservoir 21 has been depleted, or the user wishes to switch to a different cartomizer 200, for example containing a different flavor vapor precursor material, the cartomizer 200 is removed and a new cartomizer 200 is attached to the control unit 300. Accordingly, the cartomizer 200 may sometimes be referred to as a disposable portion of the e-cigarette 100, while the control unit 300 represents a re-usable portion. Alternatively, the cartomizer 200 may be configured to be refillable with e-liquid, and may require detachment from the control unit 300 for access to a filling port.

The e-cigarette 100 includes a sealing member or seal 34 disposed at a generally planar physical interface 15 between the control unit 300 and the cartomizer 200 when the two components are connected together for use. In this example the seal 34 is disposed within the control unit 300, over the control PCB 32. The seal 34 is fabricated from a resilient compressible material such as silicone, rubber, sponge, cork or a flexible plastic, and sized (along the y-axis) so as to undergo a degree of resilient compression when the cartomizer 200 and the control unit 300 are joined together and extends (along the x- and z-axes) generally to the interior of the side walls of the control unit housing 33. The seal 34 thus helps to provides a secure and close fit between the control unit 300 and the cartomizer 200 while also applying a biasing force along the y-axis (due to its resilient compression) at the mechanical interface between the cartomizer 200 and the control unit 300 when they are connected together. An outer surface of the seal 34 (i.e. the surface facing the cartomizer 200) comprises channels forming part of the fluid communication path between the air inlet/ventilation slots 24 and vaporization chamber/vapor generation chamber 17.

The seal 34 has through-apertures to receive conductive connectors in the form of the sprung pins 35 that provide electrical connection between the control unit 300 and the cartomizer 200 when coupled together as discussed further below. The sprung pins ("pogo pins") 35 are, in this example, mounted to the circuit board 32 and may be provided in accordance with conventional techniques for providing such connectors.

Figure 2:
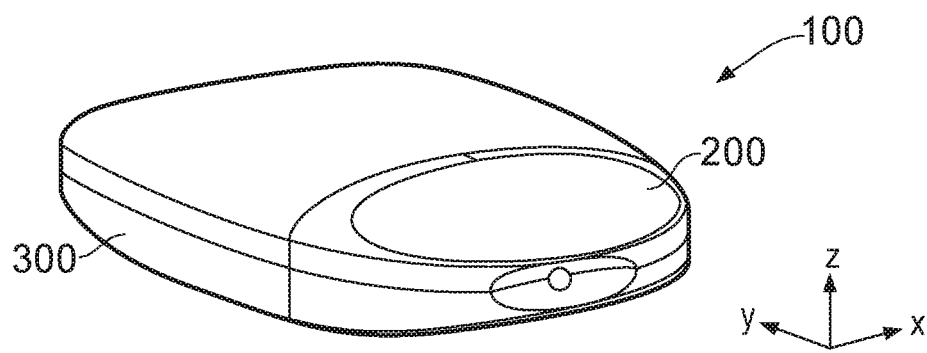
FIG. 2 schematically represents in perspective view the outer form of the vapor provision system represented in FIG. 1.

FIG. 2 is an external perspective view of the e-cigarette 100 of FIG. 1, in its assembled configuration with the cartomizer 200 coupled to the control unit 300 so that the e-cigarette 100 is ready for use. The orientation relative to the view of FIG. 1 is apparent from the representation of the xyz-axes.

Figure 3:
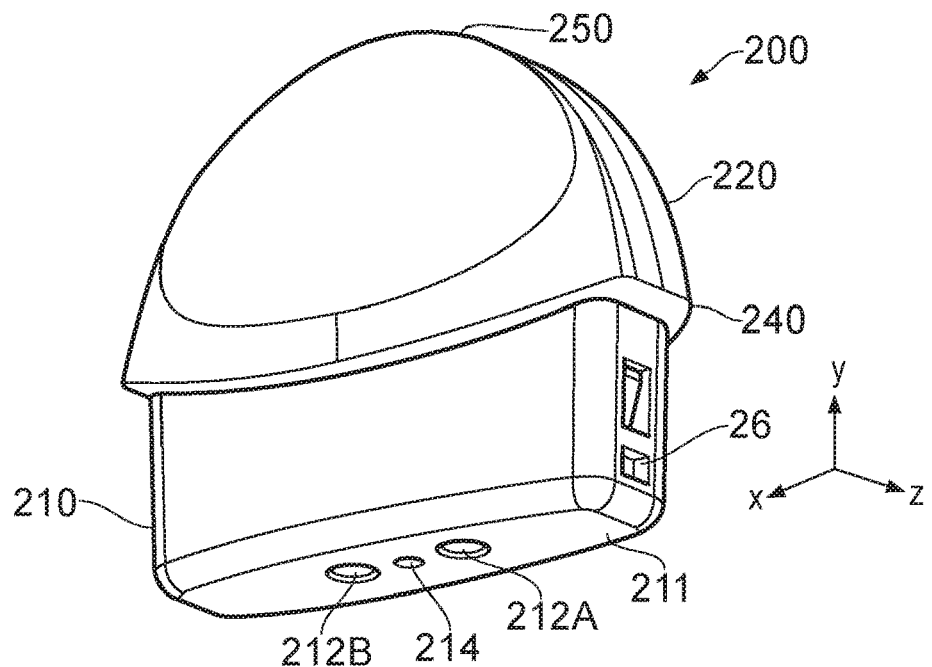
FIG. 3 schematically represents in perspective view a replaceable cartomiser part of the vapor provision system represented in FIGS. 1 and 2.

FIG. 3 is a perspective external view of the cartomizer 200 of the e-cigarette 100 of FIG. 1 in accordance with some embodiments of the disclosure. Together with FIG. 2, this external view demonstrates the depth of the cartomizer 200 (and the e-cigarette 100 as a whole), as measured parallel to the z-axis, is somewhat less than the width of the cartomizer 200 (and the e-cigarette 100 as a whole), as measured parallel to the x-axis in this specific example (although as noted above, the principles described herein are equally applicable for other sizes and shapes of vapor provision systems, for example including vapor provision systems of more conventional shapes, such as generally cylindrical systems or box-based systems).

The cartomizer 200 may, at least from an external viewpoint, be considered to comprise two main portions. In particular, there is a lower or base portion 210 and an upper portion 220 (the terms upper and lower are used here with reference to the orientation shown in FIGS. 1 and 3). The upper portion 220 is shaped to provide the mouthpiece 250 of the e-cigarette 100 and remains visible when the cartomizer 200 is connected to the control unit 300. Thus, the part of the cartomizer 200 visible in FIG. 2 is the upper portion 220.

When the cartomizer 200 is assembled with the control unit 300, the base portion 210 of the cartomizer 200 sits within (i.e. is inserted into) a correspondingly sized receptacle part in the upper part of the housing 33 of the control unit 300, and hence is not externally visible. Accordingly, and as is apparent from the figures, the depth and width of the base portion 210 are smaller than the depth and width of the upper portion 220, to allow the base portion 210 to fit inside the control unit 300. The increased depth and width of the upper portion 220 compared with the base portion 210 is provided by a lip or rim 240. When the cartomizer 200 is inserted into the control unit 300, this lip or rim 240 abuts against the top edge of the control unit housing 33. The base/floor of the receptacle part in the control unit 300 into which the base portion 210 of the cartomizer 200 is received is defined by the seal 34, with the sprung pins 35 protruding above the seal 34 (i.e. the sprung pins 35 extend into the receptacle part when a cartomizer 200 is not attached to the control unit 300).

As also shown in FIG. 3, the base portion 210 has a lower face defined by a bottom wall 211. This face abuts and compresses the sealing member 34 when the cartomizer 200 is connected to the control unit 300. The bottom wall 211 includes two larger holes 212A, 212B on either side of a smaller hole 214. The smaller hole 214 is a cartomizer air inlet hole for air inlet into the cartomizer 200 interior. That is to say, the smaller hole 214 forms part of the fluid communication path between the air inlet/ventilation slots 24 and vapor generation chamber 17 within the cartomizer 200. The larger holes 212A and 212B are electrical contact holes and are arranged to be in alignment with the sprung pins 35 when the cartomizer 200 is coupled to the control unit 300 such that the sprung pins 35 (or other contacts) pass through these holes 212A, 212B to connect with corresponding contact pads on a circuit board/contact board in the cartomizer 200 to establish an electrical interface/connection for supplying power from the battery 31 in the control unit 300 to the vaporizer/heater 22 in the cartomizer 200, as discussed further below.

When a user inhales through the mouthpiece 250 the vapor generation function of the electronic cigarette 100 is activated—i.e. electrical power is supplied to the vaporizer/heater 22. The activation of the vapor generation function may be based on conventional techniques, for example a user-activated button or an inhalation sensor, for example based around a pressure sensor/microphone arranged to detect a drop in pressure/airflow when a user inhales on the device 100, may be used. These, and other, conventional operating aspects of aerosol provision systems in accordance with the principles described herein may be provided in accordance with conventional techniques and are not described further.

As the user inhales on the mouthpiece 250, air flows into the cartomizer 200 through the air inlet hole 214 (via a pathway leading from ventilation slots 24 (see FIG. 1) defined at the juncture between the top edge of the control unit housing 33 and the cartomizer lip 240). This incoming air flows past the heater 22 (not visible in FIG. 3) which receives electrical power from the battery 31 in the control unit 300 so as to vaporize liquid from the reservoir 21 (and more especially from the wick 23). This vaporized liquid is then incorporated/entrained into the airflow through the cartomizer 200, and drawn out of the cartomizer 200 through mouthpiece 250 for inhalation by the user.

In two-part e-cigarettes comprising a separable cartomizer and control unit, it is usual to provide a mechanical connection which engages when the two components are brought into conjunction and acts to retain the components in the connected/coupled state. Devices of a cylindrical shape often use a connection arrangement that relies on a rotatory motion between the two components, such as a screw thread or a bayonet fitting. The flattened shape of the e-cigarette 100 can in some respects be considered to make a rotatable connection less practical. Consequently, the e-cigarette 100 in this example uses an alternative connection arrangement to mechanically couple the cartomizer 200 to the control unit 300, that uses a linear movement. In particular, the cartomizer 200 is configured to connect to the control unit 300 using a snap-fit arrangement.

Thus, the e-cigarette 100 comprises a pair of latching elements 40. These are labeled in FIG. 1, but can be seen more clearly in FIG. 4, which is an enlarged view of the upper part of FIG. 1. In this example there are two latching elements 40 provided at the sides of the receptacle part of the control unit 300 into which the base portion 210 of the cartomizer 200 is received for use. Each latching element 40 comprise a sprung steel element with a protrusion 44 arranged to engage with a corresponding recess 26 in the lower portion 210 of the cartomizer 200 to mechanically couple the cartomizer 200 to the control unit 300. Each latching element 40 is secured to the control unit 300 by a foot part 41 which extends into a corresponding slot in the seal 34. Compression of the seal 34 when the e-cigarette 100 is assembled squeezes the slot in the body of the seal 34 into which the foot part 41 is received to help firmly anchor the respective latch elements 40 to the control unit 300. It will of course be appreciated there are many other ways in which an appropriate mechanical coupling between the cartomizer 200 and the control unit 300 may be established.

Figure 5:
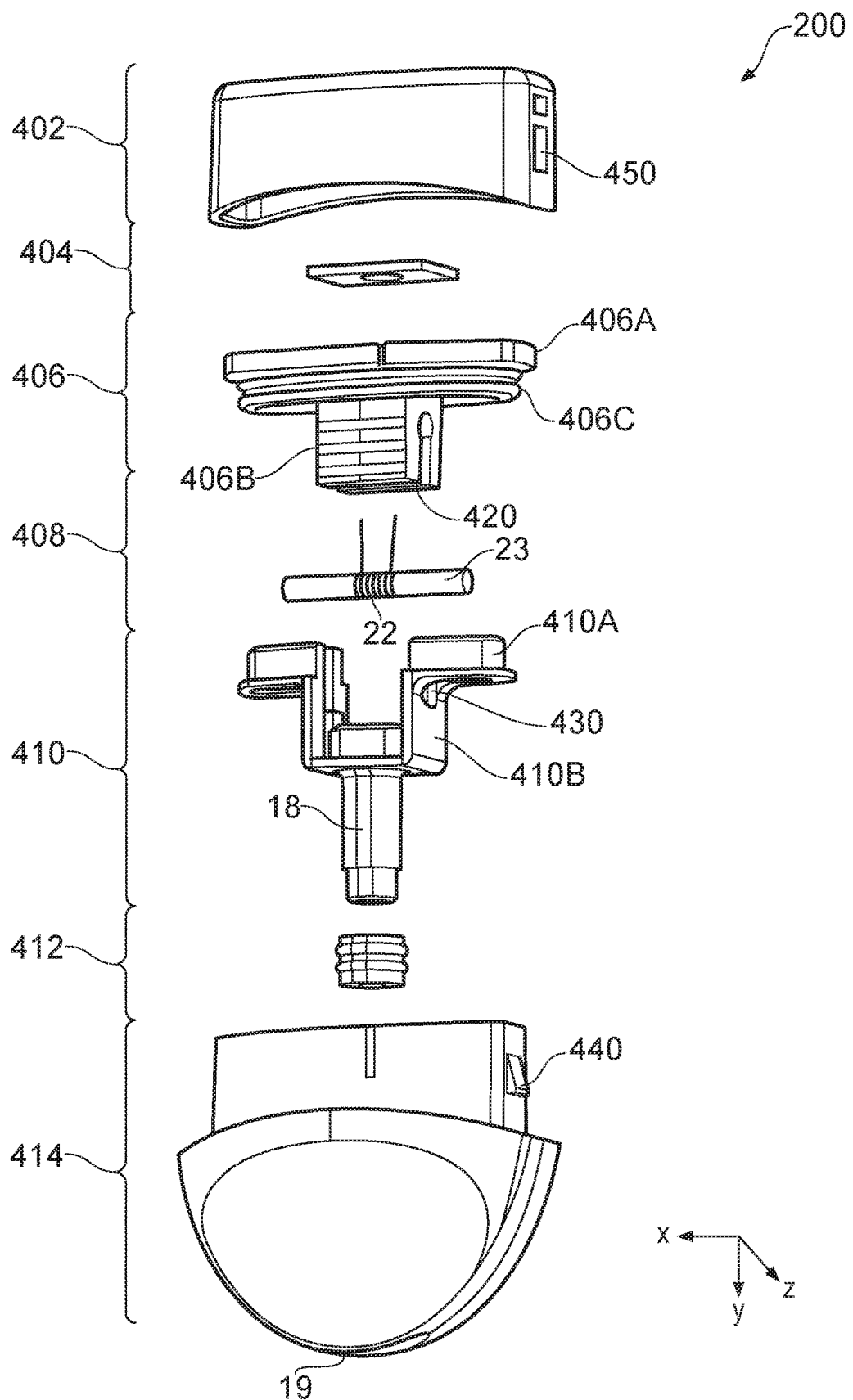
FIG. 5 schematically represents an exploded perspective view of various components of the cartomizer represented in FIG. 2.

FIG. 5 is a schematic perspective exploded view showing various components of the cartomizer 200. The orientation of the components represented in FIG. 5 is inverted with respect to orientation shown in FIGS. 1, 3 and 4.

Working down from the top of FIG. 5, the cartomizer 200 comprises a cap 402, a connection circuit board 404, a cartomizer plug 406, a wick 23 and heater 22 assembly 408, an inner frame 410, a vent seal 412, and a shell 414.

The shell 414 and cap 402 together define the outer form of the cartomizer 200, with the other elements represented in FIG. 5 being contained by the shell 414 and cap 402 when the cartomizer 200 is assembled.

The cartomizer plug 406 is a resilient member, for example comprising a silicone molding, and includes a base 406A and walls 406B extending away from the base 406A. The walls 406B at least partially define the vaporization chamber 17 in which the vaporizer (i.e. the heater 22 in this example implementation) is located when the cartomizer 200 is assembled. In this example the vaporization chamber 17 is generally cuboid. Two of the walls 406B of the cartomizer plug 406 include slots for receiving the wick 23 on which the heater 22 is wound such that the heater 22 is supported between the walls 406B of the cartomizer plug 406 (i.e. within the vaporization chamber 17) and the ends of the wick 23 extend beyond the walls 406B of the cartomizer plug 406 into the region surrounding the vaporization chamber 17.

The inner frame 410 is relatively rigid and in this example is formed from polybutylene terephthalate (PBT). The inner frame 410 includes a base 410A and walls 410B extending away from the base 410A. The base 410A of the inner frame 410 is arranged to be received in a corresponding resized receptacle portion 406C of the cartomizer plug 406 during assembly to provide a friction-fit sealed engagement between the inner frame 410 and the cartomizer plug 406. The walls 410A of the inner frame 410 contribute to defining the vaporization chamber 17 in providing an upper wall and also sidewalls that include slots 430 which cooperate with the slots 420 in the cartomizer plug 406 to help hold the wick 23 in position when the inner frame 410 is coupled to the cartomizer plug 406. The inner frame 410 further comprises a tubular wall that defines the air channel 18 that provide fluid communication between the vapor generation chamber 17 and the vapor outlet 19 provided in the mouthpiece 250.

The vent seal 412, which in this example comprises silicone, fits over the end of the air channel 18 such that, when assembled, the vent seal 412 abuts an inside surface of the shell 414 around the aerosol outlet opening 19 to provide a seal between the interior walls of the shell 414 and the air channel 18.

The shell 414, which in this example comprises polypropylene (PP), is arranged to receive the assembly comprising the cartomizer plug 406, wick and heater assembly 408, inner frame 410 and vent seal 412. The outer surface of the cartomizer plug 406 surrounding the receptacle portion 460 comprises sealing lips for providing a sealed friction fit engagement between the cartomizer plug 406 and the shell 414.

Thus, the cartomizer plug 406, inner frame 410, vent seal 412, and shell 414 together, when assembled, define the vaporization chamber 17 and air channel 18, and furthermore, a space between these elements and the inner wall of the shell 414 defines the liquid reservoir 21. As noted above, the wick 23 extends beyond the walls of the vaporization chamber 17 defined by the cooperative engagement of the cartomizer plug 406 and the inner frame 410, thereby allowing liquid in the reservoir 21 to be drawn into the vicinity of the heater 22 in the vaporization chamber 17 for vaporization, with the generated vapor being drawn out through the air channel 18 and vapor outlet 19 for inhalation by a user.

The connection circuit board (contact board) 404 in this example is a printed circuit board (PCB) and comprises conventional printed circuit board materials, for example a glass epoxy substrate with copper deposited thereon. The configuration and operation of the connection circuit board 404 is discussed further below.

During assembly, the connection circuit board 404 is received in a correspondingly sized recess 600 in the base part 406A of the cartomizer plug 406 (not visible in FIG. 5 but apparent in FIG. 6B discussed below).

The cap 402, which in this example comprises polypropylene, is arranged to cooperate with the shell 414 in a snap-fit arrangement, provided by protrusions 440 in the shell 414 cooperating with correspondingly located openings 450 in the cap 402.

Thus, when assembled the elements represented in FIG. 5 provide the cartomizer 200 as represented in FIG. 3.

Figure 6A:
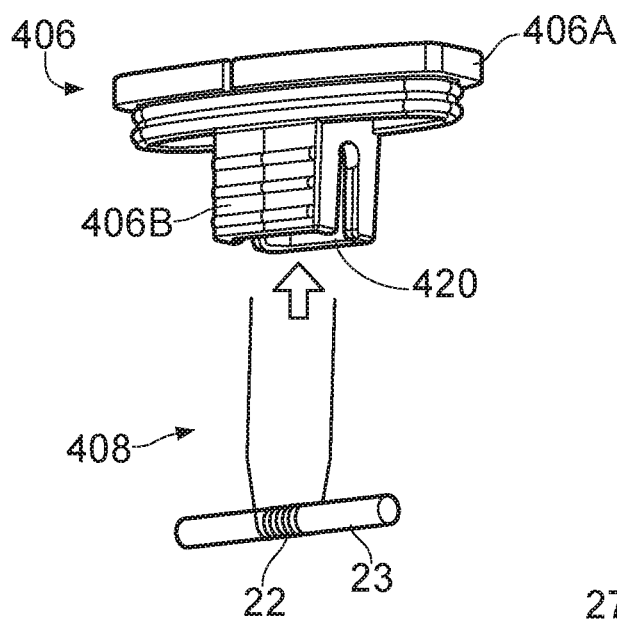
FIGS. 6A, 6B, 7 and 8 schematically represent different stages of an assembly process for the cartomizer components represented in FIG. 5.
Figure 6B:
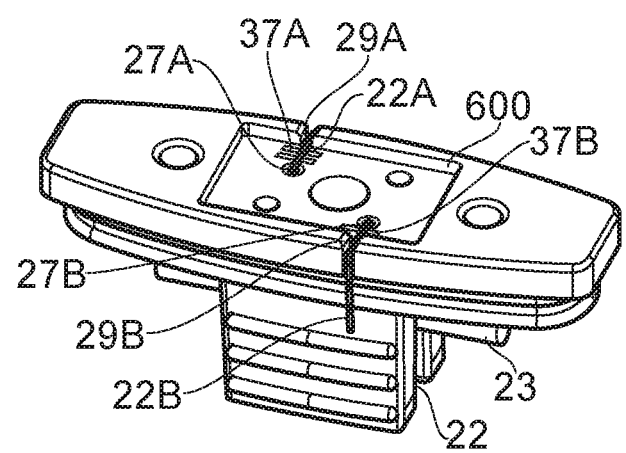

FIGS. 6A and 6B are perspective views schematically representing how the wick 23 and heater 22 assembly 408 couples to the cartomizer plug 406 during assembly of the cartomizer 200. FIG. 6A schematically shows the arrangement before the wick 23 and heater assembly is coupled to the cartomizer plug 406, and FIG. 6B schematically shows the arrangement after the wick 23 and heating assembly is coupled to the cartomizer plug 406. The view presented in FIG. 6B shows the recess 600 arranged to receive the connection circuit board 404 as discussed above (the connection circuit board itself is not shown in FIG. 6B).

As noted above, the wick 23 is received in slots 420 in the cartomizer plug 406, as schematically indicated in FIG. 6A by the arrow. The heater 22 in this example is in the form of a heating wire coiled around the wick 23 with electrical connection leads 22A and 22B for connecting electrical power to heater 22. In practice the electrical connection leads 22A, 22B may simply be continuations of the wire comprising the heater 22 wound around the wick 23. During assembly the connection leads 22A and 22B are passed through respective holes 27A, 27B in the base part 406A of the cartomizer plug 406 as the wick 23 is placed in the slots 420. The connection leads 22A, 22B thus pass out of the vaporization chamber 17 defined (at least in part) by the cartomizer plug 406 and through the base part 406A of the cartomizer plug 406 to emerge through the floor of the recess 600 in the base part 406A of the cartomizer plug 406.

The connection leads 22A, 22B are folded/bent sideward (to extend parallel to the Z-axis) where they emerge through their respective holes 27A, 27B in the floor of the recess 600 to pass through respective slots 29A, 29B in sidewalls that define the recess 600 in the cartomizer plug 406. The connection leads 22A, 22B are folded/bent again to extend down the sides of the cartomizer plug (parallel to the Y-axis), as schematically represented in FIG. 6B. Raised ridges 37A, 37B are provided in the floor of the recess 600 adjacent the portions of the respective electrical connection leads 22A, 22B which run parallel to the floor of the recess 600 act to hold these portions of the electrical connection leads a small distance away from the floor of the recess 600.

Figure 7:
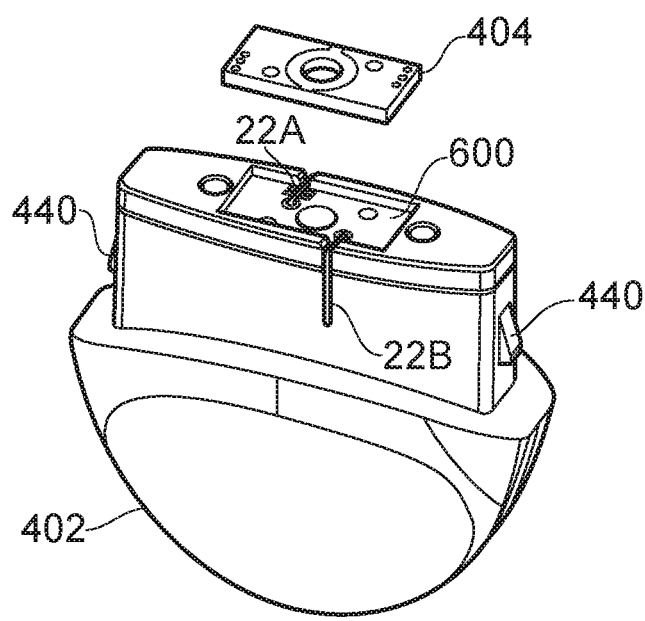

FIG. 7 is similar to, and will be understood from, FIG. 6B, but shows the cartomizer plug 406 having been received in the shell 414 of the cartomizer 200. Also shown in FIG. 7 is the connection circuit board 404 above the recess 600 into which it is received during assembly. As can be seen from FIG. 7, the recess 600 corresponds in area with the connection circuit board 404. The thickness of the connection circuit board 404 in this example is such that when placed in the recess and resting on the portions of the electrical connection leads 22A, 22B running parallel to the floor of the recess 600, the connection circuit board 404 extends slightly above the surface of the cartomizer plug 406. Accordingly, when the cap 402 is clicked into place on the shell 414 it operates to in effect press the connection circuit board 404 into the recess, and in particular, into contact with the portions of the electrical connection leads 22A, 22B running parallel to the floor of the recess 600.

Figure 8:
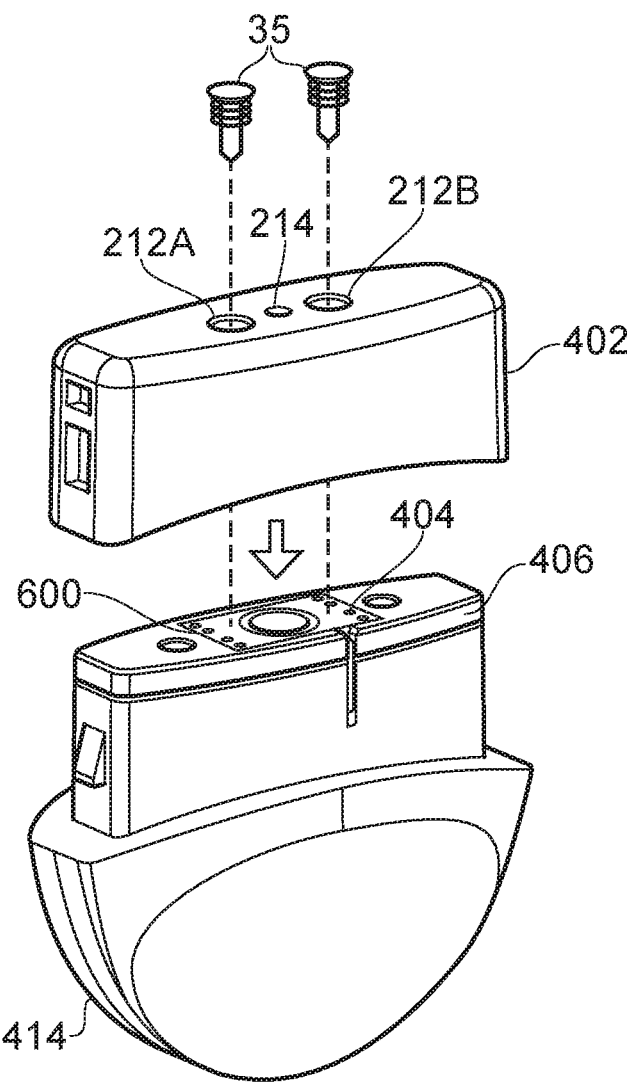

FIG. 8 is similar to, and will be understood from, FIG. 7, but shows the connection circuit board 404 received in the corresponding receptacle/recess 600 in the cartomizer plug 406, and also the cap 402 ready to be connected to the shell 414 during assembly, as schematically indicated by the arrow. Although not part of the cartomizer/cartridge 200 itself, also schematically shown in FIG. 8 are the sprung pins 35 of the device part/control unit 300 showing how the sprung pins 35 are aligned to pass though the contact opening 212A, 212B and contact the circuit board 404 when the cartridge 200 and control unit 300 are coupled together for use (as schematically indicated in FIG. 8 by the dashed lines).

Figure 9:
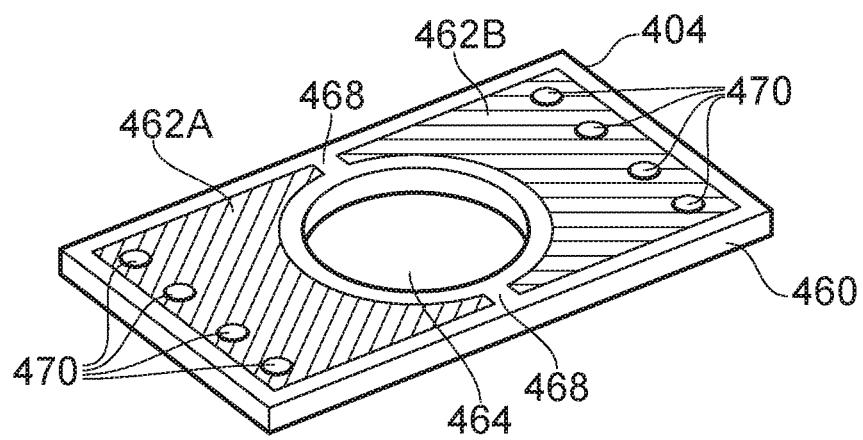
FIG. 9 schematically represents a connection circuit board of an aerosol provision system in accordance with certain embodiments of the disclosure.

FIG. 9 is a schematic perspective representation of the connection circuit board 404. As noted above, in this example the circuit board 404 comprises conventional PCB materials, such as an epoxy glass substrate 460 with copper deposit thereon. More generally, however, connection circuit board 404 may comprise any inserting substrate with conductive material arranged thereon. In FIG. 9, the outer face/side of the connection circuit board 14 (i.e. the side facing the control unit 300 in use) is shown uppermost and the deposition of copper on this surface defines two contact pads 462A, 462B, which are electrically separated from one another by gaps 468 and which together cover the majority of the surface of the circuit board 404.

As can also be seen in FIG. 9, the circuit board 404 comprises a hole 464 which, when the circuit board 404 is placed in the recess 600 in the cartomizer plug 406, aligns with an air channel connecting between the air inlet holes 214 for the cartomizer 200 and the vapor outlet opening 19, via the vapor generation chamber 17. Thus, air drawn through the cartomizer 200 by a user inhaling on the mouthpiece end 250 passes through the hole 460 in the circuit board 404 to enter the interior of the cartomizer 200. The connection circuit board (contact board) 404 in this example is a two-sided board (i.e. it comprises conductive material, e.g. copper, on both sides) with the pattern of conduct material on the inner side of the circuit board 404 (i.e. the side facing away from the control unit 300 when in use) broadly mirroring the pattern of conductive material on the outer side of the circuit board 404 represented in FIG. 9. Thus the conductive material on the inner side of the circuit board 404 also provides for two contact pads, which in this example are of a corresponding extent to the contact pads on the outer surface of the connection circuit board 404. The contact pads provided by the conductive material on the inner side of the circuit board 404 (not shown in FIG. 9) may be referred to herein as electrical contact points to help distinguish them from the contact pads provided by the conductive material on the outer side of the circuit board 404.

The contact pads 462A, 462B on the outer side of the connection circuit board 404 are respectively connected electrically to their corresponding electrical contact points on the opposing side of the connection circuit board 404 by electrical through vias 470. In the example of FIG. 9 there are four through vias 470 associated with each contact pads 462 to help reduce the resistance of this connection. It will be appreciated the through-board connection between the contact pads 462A, 462B and the corresponding contact points can be established in accordance with any conventional techniques.

When the cartomizer 200 is assembled, the circuit board 404 is sandwiched between the cartomizer plug 406 and the cap 402 such that the two contact points on the inner side of the circuit board 404 are biased into contact against respective ones of the portions of the electrical contact leads 22A, 22B running parallel to the floor of the recess 600 into which the circuit board 404 is received. The ridges 37A, 37B help with pressing the electrical connection leads 22A, 22B into good electrical contact with their corresponding connection points on the connection circuit board 404.

Furthermore, the contact pads 462A, 462B (or at least portions thereof) are arranged so as to align with respective ones of the openings 212A, 212B in the cap 402 through which the sprung pins 35 pass when the cartomizer 200 is attached to the control unit 300. Accordingly, when the cartomizer 200 is attached to the control unit 300, an electrical interface is provided by the sprung pins 35 of the control unit 300 connecting to respective ones of the contact pads 462A, 462B of the connection circuit board 404 in the cartomizer 200. The resilient sprung nature of the pins 35, in combination with the inherent resilience provided by the resilient cartomizer plug 406 in the cartomizer 200 and the seal 34 in the control unit 300 helps to ensure a positive biasing of the sprung contact pins 35 against the contact pads 462 of the circuit board 404, and also a positive biasing of the connection points on the inner side of the circuit board 404 against the corresponding portions of the electrical connection leads 22A, 22B connecting to the heater 22.

Thus, in accordance with the principles described herein, a robust and relatively simple mechanism for establishing an electrical interface between the control unit 300 and the cartomizer 200 is provided via a connection circuit board 404. The electrical interface of the example device represented in FIGS. 1 to 9 provides for two electrical contacts and may thus be used for connecting respective ends of the heater 22 to respective poles of the battery 31 via appropriate switches controlled by the control unit's control circuitry in accordance with conventional techniques.

While some particular examples have been described above, it will be appreciated there are many modifications that could be made in accordance with other implementations.

For example, the electrical interface of the example device represented in FIGS. 1 to 9 provides for two electrical contacts and may thus be used for connecting respective ends of the heater 22 to respective poles of the battery 31 (via appropriate switches controlled by the control unit's control circuitry in accordance with conventional techniques). However, in other example implementations, different numbers of connections may be provided across an interface between a control component and a cartomizer 200 in accordance with the principles described herein. For example, in some aerosol provision systems the cartomizer 200 may include additional circuitry, for example circuitry associated with measuring a temperature of the vaporizer, or sensing a liquid level in the cartomizer 200, or providing identification signaling associated with the cartomizer 200, and in these cases additional connections may be provided between the control unit 300 and the cartomizer 200 in a broadly similar manner. That is to say, in some examples a connection circuit board similar to that described herein may include more than two contact pads associated with correspondingly more than two sprung pins 35 on the control unit 300.

Furthermore, whereas in the example set out above the sprung pins are provided on the control unit 300 and the connection circuit board 404 provided on the cartomizer 200, in another implementation this arrangement could be reversed. For example, a cartomizer 200 may be provided with sprung pins 35 arranged to cooperate with contact pads of a connection circuit board 404 provided by the controlled unit 300. In this example the electrical connection points associated with the connection circuit board 404 may be used for connecting back to control circuitry in the control unit 300, as opposed to vaporizer circuitry in the cartomizer 200.

Furthermore, it will be appreciated the specific shape and configuration of the various elements discussed above may be modified for different implementations, for example in accordance with a desired overall size and shape of the electronic cigarette. For example, the system need not be generally flat, but could be more cylindrical, while still making use of the principles described herein in respect of how an electrical interface may be established between the control unit 300 and the cartomizer 200 via sprung contacts and a connection circuit board 404 arranged at an interface between the cartomizer 200 and the control unit 300.

It will further be appreciated that whereas the above-described embodiments have primarily focused on an electrical heater based vaporizer, the same principles may be adopted in accordance with vaporizers based on other technologies reliant on electrical power received from a battery across an interface between a control unit and a cartomizer, for example piezoelectric vibrator based vaporizers.

It will also be appreciated that whereas the above-described embodiments have primarily focused on liquid-based aerosol provision systems, the same principles for establishing the electrical interfaces between components can equally be applied in respect of systems for generating vapor from a solid precursor material, for example an aerosol provision system based on heating tobacco or a tobacco derivative could also make use of the principles described herein.

The connection circuit board 404 described herein is what might be referred to as a dummy circuit board in that it does not comprise any control or sensor circuitry associated with the operating functions of the aerosol provision system, but simply acts to support an appropriate electrical connection between the control unit 300 and the cartomizer 200. However, it will be appreciated that in some other example implementations, some circuitry associated with the operating functionality of the aerosol provision system 100 may be provided on a circuit board 404 that also serves to support an electrical interface between a control unit 300 and a cartomizer 200 in accordance with the principles described herein. For example, such a circuit board may include circuitry providing identification information relating to the cartomizer 200, for example for authentication or information purposes. Furthermore, such a circuit board may include sensors, such as temperature sensor, an airflow sensor or a remaining aerosol precursor level sensor for supporting the operating functions of the system.

It will be appreciated that in some cases the circuit board/contact board 404 might not comprise conventional printed circuit board materials (e.g. it might not comprise a typical PCB substrate with metallic traces deposited thereon), but could comprise other structural forms, for example any form of insulating substrate with contact pads mounted thereon. In that sense, what may for some example implementations be considered significant characteristics of the contact board are that it comprises a single insulating substrate having at least two contact pads/areas mounted thereon which are insulated from one another and arranged for use in a vapor provision system to support an electrical interface between a cartridge and a control unit when coupled together for use. For example, the contact pads may be arranged on a generally planar surface of the insulating substrate which is substantially perpendicular to a coupling axis for the cartridge and control unit (i.e. an axis along which the cartridge and control unit are brought together for coupling).

It will also be appreciated, that while the above description has focused on embodiments comprising sprung pins 35 for connecting to the contact pads 462A, 462B on the contact board (connection circuit board) 404, other example implementations might use other forms of contacts for connecting to the contact pads 462A, 462B on the contact board 404. For example, non-sprung contacts (pin-shaped or otherwise) might be used. Non-sprung contacts may in some cases be biased into contact with the contact pads 462A, 462B of the contact board 404 when the cartomizer 200 is coupled to the control unit 300 by compressive forces associated with a coupling mechanisms for attaching the cartridge to the control unit 300 and/or the inherent resilience of mounting components for the circuit board 404 and/or contacts (e.g. the cartomizer plug 406). Furthermore, in examples where the contacts are sprung contacts, they need not comprise sprung pins 35 (pogo pins), but may comprise other forms of sprung contract, for example, using metallic springs or sprung metal strips.

It will also be appreciated that there are many different ways for establishing electrical connectivity between the sprung pins 35 (or alternate contacts) and further circuitry of the aerosol provision system (e.g. power supply control circuitry if the sprung pins 35 are on the control unit side of the electrical interface or the vaporizer in the case the sprung pins 35 are arranged to provide the cartomizer 200 side of the interface). For example, in the above-described examples the sprung pins 35 are mounted to a circuit board 32 within the control device with conventional surface-mount soldering techniques. However, in other examples, the sprung pins may have a physical mounting which is separate from a connection to further circuitry of the system, which may thus be established by, for example, by flying leads/wires connected to the sprung pins 35.

Similarly, there are many different ways for establishing the electrical connectivity between the contact points on the inner side of the connection circuit board 404 and further circuitry of the aerosol provision system (e.g. the vaporizer in the case the connection circuit board 404 is arranged to provide the cartomizer 200 side of the interface, or power supply control circuitry in the case the connection board 404 is arranged to provide the control unit 300 side of the interface). For example, in the above-described examples the contact points on the inner side of the connection circuit board 404 are in biased pressed contact with the further circuitry of the cartomizer 200 (i.e. the connection leads to the vaporizer). However, in other examples the electrical connection between the connection circuit board 404 and further circuitry of the aerosol provision system may be established, for example, by soldering, or otherwise attaching, connections for the further circuitry to the contact points. That is to say, the connection between the connection circuit board 404 and further circuitry of the aerosol provision system may provide a mechanical connection as well as an electrical connection as opposed to comprising a pressed contact connection. Furthermore, in some implementations the connection circuit board 404 might not be a two-sided board, but may be a single-sided board comprising contact pads on the outside for connection to the sprung pins 35 as discussed above. In this case further circuitry of the vapor provision system, for example leads for the vaporizer, may be connected directly to the contact pads on the outer side of the connection circuit board, for example through soldering or pressed (i.e. non-soldered/brazed/welded) contact after passing through or around the board 404, rather than to contact points on an underside of the connection circuit board 404.

Furthermore, it will be appreciated the manner of cartomizer 200 assembly set out above is merely one example, and an assembly process comprising different steps, or a similar steps performed in a different order may also be adopted. For example, with reference to the steps set out in relation to FIGS. 7 and 8, in another example instead of placing the contact board 404 in its recess 600 in the cartomizer plug 406 before attaching the cap 402 to complete the cartomizer assembly (FIG. 8), the contact board 404 might first be mounted in position in the cap 402, and then the cap 402, with contact board 404 attached, connected to the shell. The contact board 404 may mount to the cap 402 friction/press fit, for example with a mounting engagement between a collar around the air inlet 214 on the cap 402 and the hole 464 through the contact board 404. In this case the cap may include locating pegs, or other guide mechanism, to help position the contact board in the cap so it is aligned with the recess 600 in the cartomizer plug 406 when the cap 402 is attached to the shell.

Figure 10:
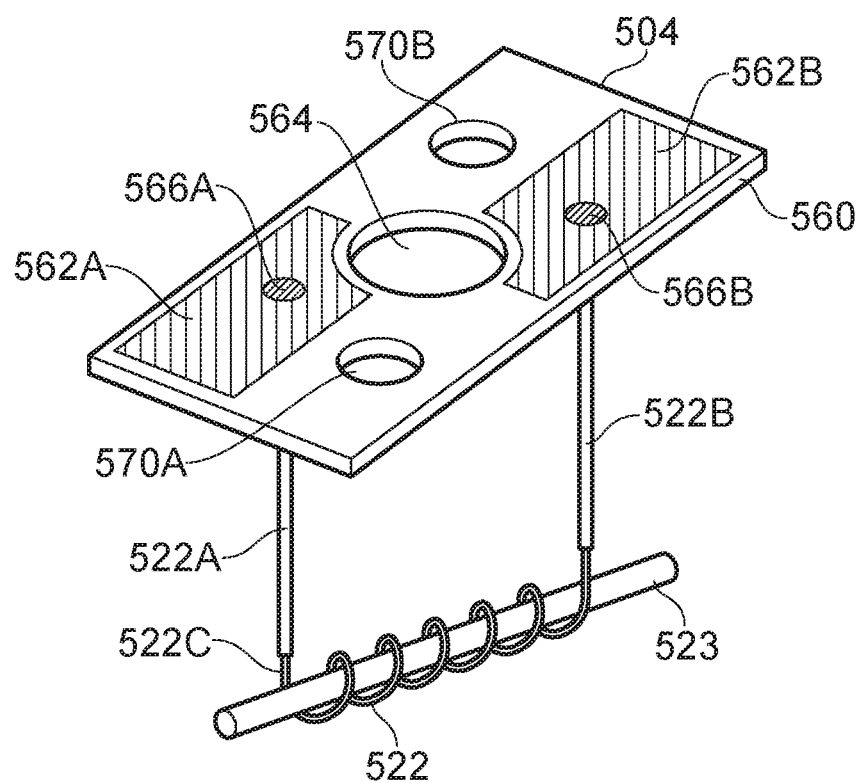
FIG. 10 schematically represents a connection circuit board of an aerosol provision system and an associated wick and heater in accordance with certain embodiments of the disclosure.

FIG. 10 schematically represents an example configuration of a connection circuit board 504 and associated wick 523 and heater 522 for use in an aerosol provision system of the kind discussed herein in accordance with certain embodiments of the disclosure. Many aspects of the connection circuit board 504, heater 522 and wick 523 represented in FIG. 10 are similar to, and will be understood from, corresponding aspects of the connection circuit board 404, heater 22 and wick 23 discussed above, and these aspects are not described again in detail in the interests of brevity. There are, however, some differences in the specific implementations of the aspects of the aerosol provision system represented in FIG. 10 which may be different from the specific implementations of corresponding aspects discussed above.

However, despite these differences in some specific implementations aspects, it will be appreciated the circuit board 504, heater 522 and wick 523 represented in FIG. 10, and the electronic aerosol provision system into which they may be incorporated, may adopt the same principles as discussed elsewhere herein in respect of how an electrical connection may be established between a cartridge part and a control unit part of an aerosol provision system. It will further be appreciated the circuit board 504, heater 522 and wick 523 may be incorporated into an aerosol provision system in a corresponding manner to that described above for the circuit board 404, heater 22 and wick 23 represented in FIGS. 1 to 9.

In the example of FIG. 10, the circuit board 504 again comprises conventional PCB materials, such as an epoxy glass substrate 560 with copper deposited thereon. More generally, however, the connection circuit board 504 may comprise any insulating substrate with conductive material arranged thereon. In FIG. 10, the outer face/side of the connection circuit board 504 (i.e. the side facing the control unit in use) is shown uppermost and the deposition of copper on this surface defines two contact pads 562A, 562B, which are electrically separated from one another. In this example the circuit board 560 is a single-layer single-sided circuit board comprising an FR4 substrate with copper deposited thereon. It will be appreciated in other examples the contact/circuit board may have different configurations, for example it may comprise different materials, and in some cases may be a two-sided circuit board. That is to say, the circuit board 560 may have conductive material (e.g. copper) deposit on both sides, and wires connecting to the contact pads 562A, 562B on one side may additionally be soldered to corresponding contact areas on the other side, for example to improve the mechanical connection between the wires and the board 504.

Unlike the contact pads 462A, 462B of the example represented FIG. 9 (which each cover around half the available upper surface of the circuit board 404), the contact pads 562A, 562B of the example represented FIG. 10 each cover around one quarter of the upper surface of the circuit board 504 in diagonally opposing quadrants. In order to contact these differently arranged contact pads 562A, 562B, it will be appreciated sprung pins in a control unit of the kind described above for contacting to the contact pads 562A, 562B will be aligned accordingly.

As can also be seen in FIG. 10, the circuit board comprises a central hole 564. This central hole 564 again aligns with an air channel of an aerosol provision system into which the circuit board 504 is incorporated for use in accordance with the principles discussed above with reference to the previous example circuit board 404 configuration represented in FIG. 9. The circuit board 504 in FIG. 10 includes two further holes 570A, 570B which are used to help locate and handle the circuit board 504 during manufacturing and assembly.

In this example implementation the circuit board 504 has dimensions of around 14 mm by 7 mm by 0.8 mm, and the copper contact pads 562A, 562B have a thickness of around 35 microns. The central hole 564 has a diameter of around 3.9 mm. The two further locating holes 570A, 570B each have a diameter of around 1.9 mm. The contact pads 562A, 562B are roughly rectangular (except where missing due to the central hole 564) with a size of around 6.1 mm by 3.4 mm. it will, of course, be appreciated these dimensions are merely for one specific implementation, and different sizes and geometries may be adopted in other implementations.

The wick 523 represented in FIG. 10 corresponds with the wick 23 discussed above, and in this regard may again comprise a glass fiber bundle.

However, whereas the heater 22 discussed above comprises a continuous wire, the heater 22 for the example represented in FIG. 10 comprises three parts/sections. These are a first lead section 522A, a second lead section 522B, and a resistive coil section 522C. The first and second lead sections 522A, 522B are electrically connected to respective ends of the resistive coil section 522C, for example using spot welding or other means. The resistive coil section 522C comprises a Cr20Ni80 alloy wire with a diameter of around 0.14 mm and is formed into a coil having seven turns with a pitch of around 0.58 mm and an inner diameter of around 2 mm, with an overall resistance of around 2.8 Ohms. The respective first and second lead sections 522A, 522B each comprise N6 Nickel wire with a diameter of around 0.25 mm and a length of around 25 mm. It will of course be appreciated these specific values relate only to one particular implementation, and other values may be adopted in other implementations. An advantage of providing a three-part configurations for the heater 522, as compared to the one-part configuration discussed above, is that the lead sections 522A, 522B may have a lower resistance per unit length than the coil section 522C. This can help avoid wasting energy in heating the lead sections of the heater 22 which are not in contact with the wick 523/liquid to be vaporized.

In the example implementation represented FIG. 10, the heater 522 is electrically connected to the respective contact pads 562A, 562B by soldering. Thus, respective ones of the heater lead sections 522A, 522B pass through holes in the circuit board 504 (not visible in FIG. 10) and are connected to respective contact pads 562A, 562B by soldering at soldering locations 566A, 566B.

As already noted, the contact circuit board 504, heater 522, and wick 523 may be incorporated into a cartomizer for an aerosol provision system in broadly the same manner as discussed above, with appropriate modifications to take account of the different configurations. For example, the arrangement of sprung contacts from the device part may be aligned slightly differently to take account of the differently-located contact pads on the circuit board 504.

Thus, and in a manner similar to that described above, when a cartomizer comprising the configuration represented in FIG. 10 is assembled, the circuit board 504 is sandwiched between a cartomizer plug and cap with the contact pads 562A, 562B (or at least portions thereof) arranged in alignment with respective openings in the cap through which sprung pins associated with a corresponding control unit pass when the cartomizer is attached to the control unit. Accordingly, when the cartomizer is attached to the control unit, an electrical interface is provided by the sprung pins of the control unit connecting to respective ones of the contact pads of the connection circuit board 504 in the cartomizer in the same manner as described above for the examples represented in FIGS. 1 to 9.

Thus, there has been described a vapor provision system comprising: a cartridge part (cartomizer) comprising a vaporizer for generating a vapor from a vapor precursor material for inhalation by a user; and a device part (control unit) comprising a power supply, such as a battery, for supplying power to the vaporizer across an electrical interface established between the cartridge part and the device part when the cartridge part is coupled to the device part for use. The electrical interface is provided by interface contacts, e.g. sprung pins, in one of the cartridge part and the device part and a contact board with contact pads in the other of the cartridge part and the device part. The sprung pins and contact pads are arranged in cooperative alignment so that respective ones of the sprung pins are in biased contact with corresponding ones of contact pads when the cartridge part is coupled to the device part for use.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A vapor provision system comprising:
a control unit and a detachable cartridge;
wherein the cartridge comprises a vaporizer for generating a vapor from a vapor precursor material for inhalation by a user; and the control unit comprises a power supply for supplying electrical power to the vaporizer across an electrical interface established between the control unit and the cartridge when the cartridge is coupled to the control unit for use; wherein the electrical interface is provided by contacts in one of the control unit or the cartridge and a contact board with contact pads in the other of the control unit or the cartridge, wherein the contacts and contact pads are arranged in cooperative alignment so that respective ones of the contacts are biased into contact with corresponding ones of contact pads when the cartridge is coupled to the control unit for use, wherein a component of the vapor provision system arranged to support the contact board in the other of the control unit or the cartridge comprises a resilient material.

2. The vapor provision system of claim 1, wherein the contact pads are on a first side of the contact board and are electrically connected to corresponding electrical contact points on a second side opposite of the first side of the contact board, and wherein electrical connections between the contact pads and further circuitry of the vapor provision system are made by electrically connecting the further circuitry to the electrical contact points.

3. The vapor provision system of claim 2, wherein the further circuitry is electrically connected to contact points on the contact board by wires in pressed contact with the electrical contact points.

4. The vapor provision system of claim 2, wherein the respective contact pads on the first side of the contact board are electrically connected to the corresponding electrical contact points on the second side of the contact board by electrical vias running through the contact board from the first side to the second side.

5. The vapor provision system of claim 2, wherein the further circuitry comprises connection leads arranged on a floor of a recess in which the contact board is arranged.

6. The vapor provision system of claim 5, wherein the connection leads enter the recess in which the contact board is arranged through openings in the floor of the recess and are bent to extend across the floor of the recess between respective ones of the electrical contact points on the second side of the contact board and the floor of the recess.

7. The vapor provision system of claim 6, wherein the floor of the recess in which the contact board is arranged comprises raised portions and the connection leads are arranged to pass between respective raised portions and contact points on the contact board.

8. The vapor provision system of claim 6, wherein the respective connection leads extend across the floor of the recess and out through side walls of the recess.

9. The vapor provision system of claim 1, wherein the contact pads are on a first side of the contact board and wherein electrical connections between the contact pads and further circuitry of the vapor provision system are made by soldering connection leads for the further circuitry to the contact pads.

10. The vapor provision system of claim 9, wherein connection leads for the further circuitry are soldered to the contact pads after passing through the contact board.

11. The vapor provision system of claim 1, further comprising a cap arranged over the contact board at a physical interface between the cartridge and the control unit, wherein the cap contains openings through which the contacts pass to contact their respective contact pads on the contact board when the cartridge is coupled to the control unit.

12. The vapor provision system of claim 1, wherein the contact board comprises a hole and is arranged about an air channel through the vapor provision system so that air is drawn though the hole in the contact board when a user inhales on the vapor provision system in use.

13. The vapor provision system of claim 1, wherein the contact pads together cover a major part of one surface of the contact board.

14. The vapor provision system of claim 1, wherein the contact board comprises further circuitry for supporting the operating functionality of the vapor provision system.

15. The vapor provision system of claim 1, wherein the contact board does not comprise further circuitry for supporting the operating functionality vapor provision system.

16. The vapor provision system of claim 1, wherein the control unit comprises the contacts and the cartridge comprises the contact board with contact pads.

17. The vapor provision system of claim 1, wherein the contact board comprises a printed circuit board (PCB).

18. The vapor provision system of claim 1, wherein the contacts comprise sprung pins.

19. A cartridge for a vapor provision system, comprising:
a vaporizer for generating a vapor from a vapor precursor material for inhalation by a user, wherein the cartridge is detachably couplable to a control unit comprising a power supply for supplying electrical power to the vaporizer across an electrical interface established between the cartridge and the control unit when the cartridge is coupled to the control unit for use; wherein the electrical interface is provided by contacts in the control unit and a contact board with contact pads in the cartridge, wherein the contacts and contact pads are arranged in cooperative alignment so that respective ones of the contacts are biased into contact with corresponding ones of contact pads when the cartridge is coupled to the control unit for use, wherein a component of the vapor provision system arranged to support the contact board in the cartridge comprises a resilient material.

20. A control unit for a vapor provision system comprising the control unit and a detachable cartridge comprising a vaporizer for generating a vapor from a vapor precursor material for inhalation by a user, the control unit comprising:
a power supply for supplying electrical power to the vaporizer across an electrical interface established between the control unit and the cartridge when the cartridge is coupled to the control unit for use; wherein the electrical interface is provided by contacts in the cartridge and a contact board with contact pads in the control unit, wherein the contacts and contact pads are arranged in cooperative alignment so that respective ones of the contacts are biased into contact with corresponding ones of contact pads when the cartridge is coupled to the control unit for use, wherein a component of the vapor provision system arranged to support the contact board in the control unit comprises a resilient material.

21. Vapor provision means comprising:
control unit means and detachable cartridge means;
wherein the cartridge means comprises vaporizer means for generating a vapor from a vapor precursor material for inhalation by a user; and the control unit means comprises power supply means for supplying electrical power to the vaporizer across electrical interface means established between the control unit means and the cartridge means when the cartridge means is coupled to the control unit means for use; wherein the electrical interface means is provided by contact means in one of the control unit means or the cartridge means and contact board with contact pad means in the other of the control unit means or the cartridge means, wherein the contact means and contact pad means are arranged in cooperative alignment so that respective ones of the contact means are biased into contact with corresponding ones of contact pad means when the cartridge means is coupled to the control unit means for use, wherein a component of the vapor provision means arranged to support the contact board in the other of the control unit and the cartridge comprises a resilient material.

22. A method of establishing an electrical connection between a control unit and a detachable cartridge in a vapor provision system, the method comprising:
providing one of the control unit or the detachable cartridge with contacts and the other of the control unit or the detachable cartridge with a contact board with contact pads, wherein a component of the vapor provision system arranged to support the contact board in the other of the control unit or the cartridge comprises a resilient material, wherein the contacts and contact board are arranged so the contacts and contact pads are in cooperative alignment so that respective ones of the contacts are biased into contact with corresponding ones of contact pads when the cartridge is coupled to the control unit for use; and
coupling the cartridge to the control unit to establish the electrical connection.

* * * * *

UNITED STATES PATENT AND TRADEMARK OFFICE
CERTIFICATE OF CORRECTION

PATENT NO. : 11,123,501 B2  
APPLICATION NO. : 16/087000  
DATED : September 21, 2021  
INVENTOR(S) : Nettenstrom It is certified that error appears in the above-identified patent and that said Letters Patent is hereby corrected as shown below:

In the Claims

Column 18, Line 46, Claim 12 delete "drawn though the" and insert --drawn through the--

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*